US006458872B1

(12) United States Patent
Ravichandran et al.

(10) Patent No.: US 6,458,872 B1
(45) Date of Patent: Oct. 1, 2002

(54) BENZOTRIAZOLE UV ABSORBERS HAVING ENHANCED DURABILITY

(75) Inventors: Ramanathan Ravichandran, Nanuet, NY (US); Joseph Suhadolnik, Yorktown Heights, NY (US); Mervin G. Wood, Poughquag, NY (US); Anthony Debellis, Garnerville, NY (US); Robert E. Detlefsen, Putnam Valley, NY (US); Revathi Iyengar, Courtland Manor, NY (US); Jean-Pierre Wolf, Courtaman (CH)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 0 days.

(21) Appl. No.: 09/851,453

(22) Filed: May 8, 2001

Related U.S. Application Data

(60) Division of application No. 09/614,527, filed on Jul. 12, 2000, now Pat. No. 6,262,151, which is a division of application No. 09/234,880, filed on Jan. 21, 1999, now Pat. No. 6,166,218, which is a continuation-in-part of application No. 08/961,127, filed on Oct. 30, 1997, now Pat. No. 5,977,219.

(51) Int. Cl.$^7$ .................................. C08K 5/3475
(52) U.S. Cl. ....................... 524/89; 524/91; 524/94
(58) Field of Search ..................... 524/89, 91, 94

(56) References Cited

U.S. PATENT DOCUMENTS

| | | | |
|---|---|---|---|
| 3,936,305 A | 2/1976 | Hiraishi et al. | 96/84 |
| 4,082,679 A | 4/1978 | Rhodes | 252/8.8 |
| 4,226,763 A | 10/1980 | Dexter et al. | 260/45.8 |
| 4,275,004 A | 6/1981 | Winter et al. | 260/206 |
| 4,278,589 A | 7/1981 | Dexter et al. | 260/45.8 |
| 4,315,848 A | 2/1982 | Dexter et al. | 260/45.8 |
| 4,347,180 A | 8/1982 | Winter et al. | 260/206 |
| 4,681,905 A | 7/1987 | Kubota et al. | 524/91 |
| 4,684,679 A | 8/1987 | Kubota et al. | 524/91 |
| 4,684,680 A | 8/1987 | Kubota et al. | 524/91 |
| 4,868,246 A | 9/1989 | MacLeay et al. | 525/142 |
| 5,106,891 A | 4/1992 | Valet | 524/91 |
| 5,108,835 A | 4/1992 | Hähnsen et al. | 428/334 |
| 5,166,355 A | 11/1992 | Leistner et al. | 548/260 |
| 5,250,698 A | 10/1993 | Falk et al. | 548/260 |
| 5,278,314 A | 1/1994 | Winter et al. | 548/259 |
| 5,280,124 A | 1/1994 | Winter et al. | 548/259 |
| 5,292,890 A | 3/1994 | Moshchitsky et al. | 548/260 |
| 5,360,850 A | 11/1994 | Moshchitsky et al. | 524/91 |
| 5,436,349 A | 7/1995 | Winter et al. | 548/259 |
| 5,516,914 A | 5/1996 | Winter et al. | 548/259 |
| 5,554,760 A | 9/1996 | Winter et al. | 548/260 |
| 5,563,242 A | 10/1996 | Winter et al. | 524/91 |
| 5,574,166 A | 11/1996 | Winter et al. | 548/260 |
| 5,607,987 A | 3/1997 | Winter et al. | 524/91 |
| 5,646,088 A | 7/1997 | Hada et al. | 503/209 |

FOREIGN PATENT DOCUMENTS

| | | |
|---|---|---|
| DE | 116230 | 11/1961 |
| DE | 1670951 | 2/1971 |
| EP | 0453396 | 10/1991 |
| EP | 0593936 | 4/1994 |
| EP | 0652210 | 5/1995 |
| EP | 0698637 | 2/1996 |
| EP | 0750224 | 12/1996 |
| GB | 1287770 | 9/1972 |
| GB | 2311143 | 9/1997 |
| GB | 2319035 | 5/1998 |
| JP | 47-15210 | 5/1972 |
| JP | 53047453 | 4/1978 |
| JP | 3-57690 | 3/1991 |

OTHER PUBLICATIONS

Chem. Abstr. vol. 77, No. 24, 153215, (1974) for JP 7215210.
Abstract for EP 065210 (1995).
J. March, "Advanced Organic Chemistry", 2$^{nd}$ Ed., Chapter 9, (1977), p. 253.
J. L. Gerlock et al., Proc. 36$^{th}$ Annual Tech. Sym., Cleveland Coating Society, May 18, 1993, "Learning to Anticipate the Weatherability Performance of Automotive Paint Jobs—UVA Loss" Chem. Abstr. 84:151415 for Vysokomol. Soedin., Ser. A, 18(3), pp. 553–556, (1976).
J. Pickett et al., Angew. Macromol. Chem., vol. 232, (1995), pp. 229–238.
J. Catalán et al., J. Am. Chem. Soc., (1992), vol. 114, pp. 964–966.
H. Heller., Eur. Polymer J. Suppl., 1969, pp. 105–132.
Chem. Abstr. 1978:512111 for JP 53047453 (1978).

Primary Examiner—Deborah C. Lambkin
(74) Attorney, Agent, or Firm—Tyler A. Stevenson; Luther A. R. Hall

(57) ABSTRACT

Benzotriazole UV absorbers which are substituted at the 5-position of the benzo ring by an electron withdrawing group exhibit enhanced durability and very low loss rates when incorporated into automotive coatings. This is particularly the case when the 3-position of the phenyl ring is also substituted by phenyl or phenylalkyl such as α-cumyl. Compounds where the 5-position of the benzo ring are substituted by perfluoroalkyl such as trifluoromethyl are particularly of interest for both their enhanced durability and for their excellent solubility and excellent color properties in some thermoplastic compositions when the phenyl ring is substituted at the 3-position by hydrogen or tert-alkyl.

13 Claims, No Drawings

BENZOTRIAZOLE UV ABSORBERS HAVING ENHANCED DURABILITY

This application is a divisional of application Ser. No. 09/614,527, filed Jul. 12, 2000, U.S. Pat. No. 6,262,151, which is a divisional of application Ser. No. 09/234,880, filed Jan. 21, 1999, now U.S. Pat. No. 6,166,218, which is a continuation-in-part of application Ser. No. 08/961,127, filed on Oct. 30, 1997, now U.S. Pat. No. 5,977,219, which application claims the benefit under 35 USC 119(e) of U.S. application Ser. No. 08/745,146, filed on Nov. 7, 1996, and converted into a Provisional Application by petition under 37 CFR 1.53(b)(2)(ii), filed on May 23, 1997, and granted on Aug. 7, 1997.

Benzotriazole UV absorbers being substituted in the benzo ring by electron withdrawing moieties exhibit enhanced durability and low loss rates when incorporated into automotive coatings and thermoplastic compositions.

BACKGROUND OF THE INVENTION

The benzotriazoles have long been an important class of UV absorbers and have gained wide commercial importance and acceptance for many industrial applications. The prior art is replete with references to their manufacture and utility. However, as requirements become ever more stringent and demanding, the search for still more stable and durable benzotriazoles continues. The gradual phase out of HAPS solvents, such as xylene, because of environmental concerns and their replacement with non-HAPS solvents, such as esters, ethers or ketones, and increased durability requirements for automotive coatings make this search more urgent Indeed, the automotive industry is most concerned about UVA losses from automotive paints and coatings as seen in the publication by J. L. Gerlock et al., Proc. 36th Annual Tech. Sym. (Cleveland Coating Society), May 18, 1993.

Vysokomol Soedin, Ser. A, 18(3), 553 (1976) describes the linear dependence of hydrogen bond strength and photostability in benzotriazoles.

J. E. Pickett et al., Angew. Makromol. Chem. 232, 229 (1995) describe the photodegradation of benzotriazole UV absorbers in poly(methyl methacrylate) films. Structural variation generally caused only small differences in the rates of degradation unless the substitution disrupted the intramolecular hydrogen bonds which are critical for stability. Pickett et al. did not test any benzotriazoles containing both electron withdrawing and electron donating groups as in the instant invention.

J. Catalan et al., J. Am. Chem. Soc., 114, 964 (1992) and H. J. Heller, Eur. Polymer J. Suppl. 1969, 105 both suggest that a bulky substituent such as tert-butyl ortho to the hydroxy group on the phenyl ring will increase stability in highly polar systems.

The prior art leads one to the conclusion that strengthening the hydrogen bond leads to a more stable benzotriazole, but does not teach how this can be accomplished. The instant invention discloses benzotriazoles which exhibit enhanced durability, but surprisingly this enhanced durability is not always related to greater hydrogen bond strength. Indeed, compounds with enhanced durability often have weaker, not stronger hydrogen bonds.

U.S. Pat. Nos. 4,226,763; 4,278,589; 4,315,848; 4,275,004; 4,347,180; 5,554,760; 5,563,242; 5,574,166 and 5,607,987 describe selected benzotriazoles, substituted in the 3-position of the hydroxyphenyl ring by an α-cumyl group, which show very good durability in automotive coatings. These benzotriazoles represent the present state of the art.

The instant invention is directed at preparing benzotriazoles which exhibit still better durability and low loss rates from the prior art benzotriazoles.

U.S. Pat. Nos. 5,278,314; 5,280,124; 5,436,349 and 5,516,914 describe red-shifted benzotriazoles. These benzotriazoles are substituted in the 3-position of the phenyl ring with an α-cumyl group and at the 5-position of the benzo ring by thio ethers, alkylsulfonyl or phenylsulfonyl moieties. Red-shifting the benzotriazoles is desirable for spectral reasons. A group at the 5-position which is also electron withdrawing provides additional benefits in low loss rates and durability as found in the instant invention. Missing from these patents are any alkylsulfones with seven or fewer carbon atoms. When such sulfonyl substituents are combined with specifically α-cumyl moieties, extremely durable compounds result which, due to the bulk of the α-cumyl moiety have sufficiently low volatility to be useful in coating and other polymer systems.

The presence of an α-cumyl or phenyl group ortho to the hydroxy group on the phenyl ring exerts a surprisingly large positive effect on benzotriazole photostability in coatings and photographic gel systems. The magnitude of this effect, particularly when compared to a tert-butyl group in that position, is well beyond prediction. The combination of both an electron withdrawing group on the benzo ring and an α-cumyl or phenyl group on the phenyl ring in the same molecule leads to extremely desirable properties in coating systems when high UV absorber permanence is critical.

Novel compounds meeting these parameters as being extremely stable in aggressive use environments constitute a first portion of this invention.

The presence of the electron withdrawing moiety at the 5-position of the benzo ring has a powerful stabilizing effect on benzotriazoles in general and is observed in other polymer systems such as polycarbonate and poly(vinyl chloride) substrates as well. However, the effect of having an α-cumyl or phenyl group ortho to the hydroxy moiety on the phenyl ring is much smaller to non-existent in some polymer systems such as polycarbonate or poly(vinyl chloride) even though critical for coating systems as described above.

In addition to being more photostable, the compounds of this invention are red-shifted, absorbing strongly in the 350–400 nm wavelength range. While such red-shifting is desirable in that a greater portion of the UV spectrum is absorbed, this can also introduce color if the absorption beyond 400 nm is significant. This can limit the use of such compounds, particularly in systems such as polycarbonate glazing applications or present difficulties in various pigmented systems.

It is found that the nature of the substituent ortho to the hydroxyl group on the phenyl ring has an unexpected impact on color imparted to the substrate by the benzotriazole. Thus, relatively subtle differences in substitution on the phenyl ring can have a large impact on the resulting color and the applicability of the benzotriazole in specific color sensitive applications. There are striking differences between having hydrogen, alkyl or α-cumyl at this 3-position.

Furthermore, it is found that, when the 5-position of the benzo ring is substituted with a trifluoromethyl group, the resulting benzotriazole not only exhibits the same or greater enhanced stability when incorporated into thermoplastic resins, but also imparts less color than related benzotriazoles substituted at the 5-position with other electron withdrawing moieties such as sulfonyl or carbonyl. These trifluoromethyl compounds also absorb strongly in the 350–400 nm wavelength range despite the low color and are extremely compatible in a wide range of substrates such as acrylic resins, hydrocarbons, polycarbonates and poly(vinyl chloride).

There are a multitude of general references to benzotriazoles having in the 5-position of the benzo ring electron withdrawing groups such as esters, amides, sulfones and the like that are not substituted in the 3-position of the phenyl ring by an α-cumyl or phenyl moiety. In many of these references the broadly described compounds are unexemplified and no teaching or appreciation taught of the positive effect on photostability described in this invention. In any event, the vast majority of these structures fall well outside the scope of instant invention.

Perfluoroalkyl, specifically trifluoromethyl, is an ideal substituent for the 5-position of the benzo ring. The prior art relevant to this substituent is very limited and exemplifies none of the instant compounds. As a result, said prior art naturally fails to point out the important advantages regarding stability, color and compatibility achievable with the 5-trifluoromethyl substituted benzotriazoles of this invention. The general, unexemplified references to alkyl substituted with halogen are acknowledged, but are clearly irrelevant to the instant invention.

German Offen. 1,670,951 describes inter alia the use of methylene (or alkylidene) bis-benzotriazoles substituted with electron withdrawing groups in polymeric resins. Especially useful are the asymmetrical compounds where only one benzotriazole moiety is substituted. Such asymmetric compounds have considerably less color.

German 116,320 provides a method of preparing benzotriazole N-oxide intermediates which can be converted into dyes and light stabilizers. The N-oxide of 5-trifluoromethyl-2-(2-hydroxy-5-methylphenyl)-2H-benzotriazole is disclosed. This N-oxide could be reduced to the corresponding benzotriazole which is substituted at the 5-position of the phenyl ring. However, this benzotriazole is clearly outside the scope of the instant claims. Other related light stabilizer intermediates are generically disclosed in this reference, but none where ever converted to actual benzotriazole UV absorbers. The outstanding properties of such benzotriazole UV absorbers clearly went undiscovered.

Japanese Hei 3-57690 claims a color developer sheet compositions containing salicylic acid salts and benzotriazoles. Broadly described are benzotriazoles which may be substituted on the benzo ring with unspecified trihalomethyl. However, other benzotriazole ring substituents also are broadly described to include unspecified alkyl, alkoxy, aryloxy, amino, cyano, acyl, nitro and halogen. The only benzotriazoles named as typical examples are either unsubstituted on the benzo ring or substituted by chlorine. The preference is for liquid compounds. The 3-position of the phenyl ring is specified as tert-alkyl. While this reference broadly discloses a wide variety of benzotriazole derivatives in its photographic compositions many are electron donating and produce compounds which are in photostability inferior not only to the instant compounds, but also to standard unsubstituted benzotriazoles. No examples or differentiation between within this diverse array is seen. Further, while generic trihalomethyl is described, no compounds of this description are shown or further described in any way. Additionally, trichloro, tribromo and triiodo compounds are clearly outside the scope of the instant invention.

Japanese Sho 47-15210 describes resin compositions containing selected benzotriazoles substituted by a fluorinated alkyl. The generic structures allows for a fluorinated alkyl, but not necessarily perfluorinated alkyl, to be added to either or both the benzo or phenyl rings at any position (the substituents are floating in the generial formula). Non-fluorinated substituents, one on each ring, are defined as hydrogen, halogen, hydroxy, alkyl and alkoxy with no other more specific description. The exemplified resins are poly(vinyl chloride), polycarbonate, ABS and nylon. Seven compounds are specifically exemplified all outside the scope of the instant invention plus one composition containing 2-(2-hydroxy-5-methylphenyl)-2H-benzotriazole. No physical data or synthesis for any of these seven compounds are given.

The seven compounds exemplified in the Japanese reference are given below:

a. 2-(2-hydroxy-4-trifluoromethylphenyl)-2H-benzotriazle;
b. 5-methyl-2-(2-hydroxy-4-trifluoromethylphenyl)-2H-benzotriazole;
c. 5-methoxy-2-(2-hydroxy-4-trifluoromethylphenyl)-2H-benzotriazole;
d. 5-chloro-2-(2-hydroxy-4-trifluoromethylphenyl)-2H-benzotriazole;
e. 5-peroxymethoxy-2-(2-hydroxy-4-methylphenyl)-2H-benzotriazole;
f. 5-perfluorooctyl-2-(2-hydroxy-4-methylphenyl)-2H-benzotriazole; and
g. 5-perfluorooctyl-2-(2-hydroxy-4-trifluoromethylphenyl)-2H-benzotriazole.

There are several distinct differences between the disclosure of this Japanese reference and the instant invention. First all the exemplified compounds of the Japanese reference are substituted in the 4-position of the phenyl ring by groups other than hydrogen. The reference allows for substitution of either fluoroalkyl or fluoroalkoxy on any site on either ring as a means of providing for an improved UV absorber. Data given in this application shows this teaching to be inaccurate. Electron withdrawing moieties on the phenyl ring as found in a, b, c, d, and g above, are shown to provide compounds with less durability than unsubstituted derivatives as seen in Example 77. Spectral coverage in the red region is also compromised as seen in Example 74. Significantly, 2-(2-hydroxy-5-trifluoromethylphenyl)-2H-benzotriazole which is very similar to compound a above, is blue-shifted relative to benzotriazoles such as 2-(2-hydroxy-5-methylphenyl)-2H-benzotriazole as seen in Example 74. Blue-shifting is undesirable since the need for coverage in the 350–400 nm region is critical for UV absorbers.

An electron donating group at the 5-position of the benzo ring such as the ether compound c above reduces stability as seen in Example 77. While the Japanese reference states fluoroalkyl or fluoroalkoxy radical leads to enhanced stability under light, the instant invention shows that it is the electron withdrawing nature of the group at the 5-position on the benzo ring that confers greater photostability. No such inference in seen in the Japanese reference, and the electron donating ether even a fluorinated ether is counterindicated for enhanced stability.

Furthermore, all examples in the Japanese reference bear only one substituent on the phenyl ring and that is specifically at the 4-position. The instant invention specifically claims only hydrogen at the 4-position as substitution at the 4-position brings undesirable consequences for the use of these compounds in many applications. The compound f is the closest to the instant invention, but it is substituted by a 4-methyl group. As seen in Example 79, substitution of the phenyl ring by an electron donating group at the 5-position diminishes photostability in coatings. Pickett et al. report the same loss of durability for such compounds in thermoplastics. The electron donating characteristics of methyl are less pronounced, but are still similar to alkoxy. The $\sigma_p$ value, as measure of the electronic effect of substituents for aromatic methoxy substitution is −0.27 while for methyl is −0.17 (March J. "Advanced Organic Chemistry", 2nd Ed (1977), McGraw-Hill, New York, p 253).

While the generic disclosure of the Japanese reference overlaps formula I of the instant application no such compound is specifically disclosed in the Japanese reference. As mentioned above, all examples of the Japanese reference are substituted at the 4-position of the phenyl ring, most contain the electron withdrawing $CF_3$ group at the 4-position. Compounds of the instant invention explicitly denote hydrogen at the 4-position of the phenyl ring for reasons including color and stability, and expressly designate the 5-position of the benzo ring as the location of the perfluoroalkyl moiety for reasons of stability and spectral coverage.

U.S. Pat. Nos. 3,936,305; 4,681,905; 4,684,679; 4,684,680 and 5,108,835 teach the 2,2'-methylene-bis[4-hydrocarbyl-6-(benzotriazol-2-yl)phenols] having high molar activities and low volatility. In addition U.S. Pat. Nos. 5,292,890 and 5,360,850 teach that asymmetrical bis-benzotriazoles display higher solubility in organic non-polar solvents that the symmetrical dimers made from the same benzotriazole monomer.

U.S. Pat. No. 5,166,355 describes a process for making 2,2'-methylene-bis[6-(benzotriazol-2-yl)-4-hydrocarbylphenol] or 5,5'-methylene-bis(2-hydroxy-4-alkoxybenzophenone) using bis(dialkylamino)methane.

Related bis-benzotriazoles of the instant invention substituted at one or at both of the benzotriazole rings by perfluoroalkyl are unknown and provide the same improvement to these bis-benzotriazoles as mentioned above, namely enhanced durability and broader spectral coverage. Substitution of only one of the benzotriazole moieties in these bis-benzotriazoles by perfluoroalkyl gives the additional advantage of much lower color than the disubstituted compound, indeed nearly to the color of the bis-benzotriazole not substituted by perfluoroalkyl.

DETAILS OF THE DISCLOSURE

The instant invention pertains to novel benzotriazole UV absorbers having enhanced stability and durability and a low loss rate when incorporated into automotive coatings. These new benzotriazole UV absorbers are also soluble in a variety of substrates including thermoplastic polymers and often are essentially colorless even though absorbing in the 350–390 nm range.

More specifically, the instant invention pertains to new benzotriazole compounds of formula I, I, II or IV

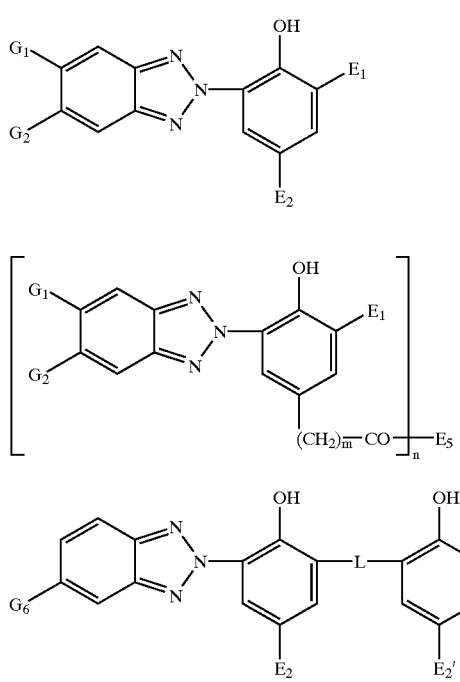

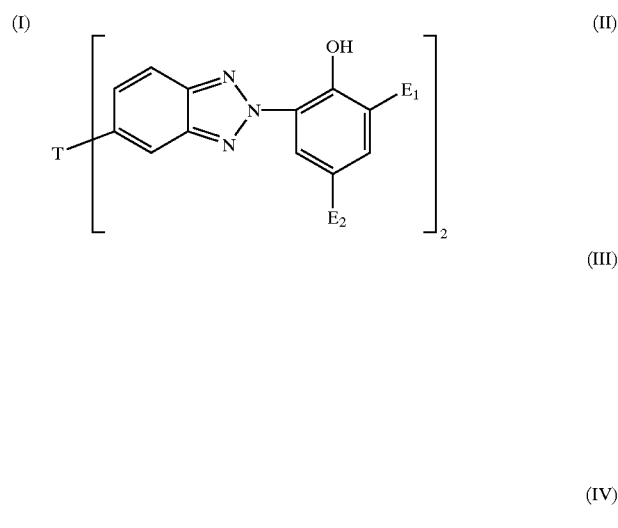

wherein
$G_1$ is hydrogen or chloro,
$G_2$ is cyano, perfluoroalkyl of 1 to 12 carbon atoms, fluoro, —CO—$G_3$, —COO$G_3$, —CONH$G_3$, —CON($G_3$)$_2$, $E_3$SO— or $E_3$SO$_2$—,
$G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms,
$G_6$ is perfluoroalkyl of 1 to 12 carbon atoms,
$G_7$ is hydrogen or perfluoroalkyl of 1 to 12 carbon atoms,
$E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $E_1$ is alkyl of 1 to 24 carbon atoms substituted by one or two hydroxy groups,
$E_2$ and $E_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ and $E_2'$ are independently said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where $E_4$ is straight or branched chain alkyl of 1 to 24 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof;

n is 1 or 2, when n is 1, $E_5$ is Cl, OE$_6$ or NE$_7$E$_8$, or $E_5$ is —PO(OE$_{12}$)$_2$, —OSi(E$_{11}$)$_3$ or —OCO—E$_{11}$, or straight or branched chain $C_1$–$C_{24}$alkyl which is interrupted by —O—, —S— or —NE$_{11}$ and which can be unsubstituted or substituted by —OH or —OCO—E$_{11}$, $C_5$–$C_{12}$ cycloalkyl which is unsubstituted or substituted by —OH, straight chain or branched $C_2$–$C_{18}$alkenyl which is unsubstituted or substituted by —OH, $C_7$–$C_{15}$aralkyl, —CH$_2$—CHOH—E$_{13}$ or glycidyl, $E_6$ is hydrogen, straight or branched chain $C_1$–$C_{24}$alkyl which is unsubstituted or substituted by one or more OH, OE$_4$ or NH$_2$ groups, or —OE$_6$ is —(OCH$_2$CH$_2$)$_w$OH or —(OCH$_2$CH$_2$)$_w$OE$_{21}$ where w is 1 to 12 and $E_{21}$ is alkyl of 1 to 12 carbon atoms, $E_7$ and $E_8$ are independently hydrogen, alkyl of 1 to 18 carbon atoms, straight or branched chain $C_3$–$C_{18}$alkyl which is interrupted by —O—, —S— or —NE$_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring, or $E_5$ is —X—(Z)$_p$—Y—E$_{15}$ wherein X is —O— or —N(E$_{16}$)—, Y is —O— or —N(E$_{17}$)—, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is zero, 1 or 2, is 1, or p is also zero when X and Y are —N(E$_{16}$)— and —N(E$_{17}$)—, respectively, $E_{15}$ is a group —CO—C(E$_{18}$)=C(H)E$_{19}$ or, when Y is —N(E$_{17}$)—, forms together with E$_{17}$ a group —CO—CH=CH—CO—, wherein E$_{18}$ is hydrogen or methyl, and $E_{19}$ is hydrogen, methyl or —CO—X—E$_{20}$, wherein $E_{20}$ is hydrogen, $C_1$–$C_{12}$-alkyl or a group of the formula

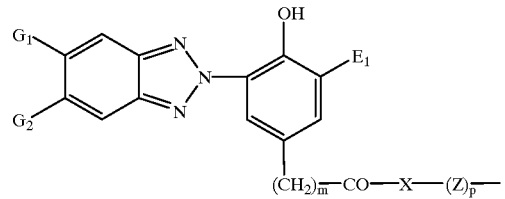

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, when n is 2, $E_5$ is one of divalent radicals —O—E$_9$—O— or —N(E$_{11}$)—E$_{10}$—N(E$_{11}$)—, $E_9$ is $C_2$–$C_8$alkylene, $C_4$–$C_8$alkenylene, $C_4$alkynylene, cyclohexylene, straight or branched chain $C_4$–$C_{10}$alkylene which is interrupted by —O— or by —CH$_2$—CHOH—CH$_2$—O—E$_{14}$—O—CH$_2$—CHOH—CH$_2$—, $E_{10}$ being straight or branched chain $C_2$–$C_{12}$alkylene which may be interrupted by —O—, cyclohexylene, or

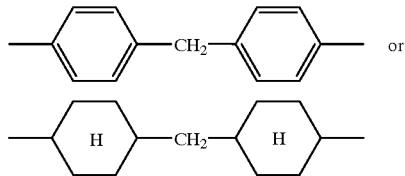

or $E_{10}$ and $E_{11}$ with the two nitrogen atoms form a piperazine ring, $E_{14}$ is straight or branched chain $C_2$–$C_8$alkylene, straight or branched chain $C_4$–$C_{10}$alkylene which is interrupted by —O—, cycloalkylene, arylene or

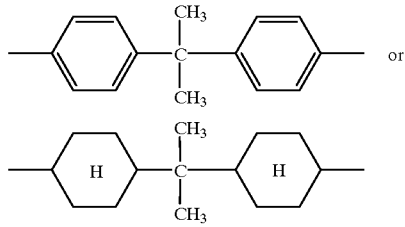

where $E_7$ and $E_8$ are independently hydrogen, alkyl of 1 to 18 carbon atoms or $E_7$ and $E_8$ together are alkylene of 4 to 6 carbon atoms, 3-oxapentamethylene, 3-iminopentamethylene or 3-methyliminopentamethylene, $E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, $E_{13}$ is H, straight chain or branched $C_1$–$C_{18}$alkyl which is substituted by —PO(OR$_{12}$)$_2$, phenyl which is unsubstituted or substituted by OH, $C_7$–$C_{15}$aralkyl or —CH$_2$OE$_{12}$, $E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, L is alkylene of 1 to 12 carbon atoms, alkylidene of 2 to 12 carbon atoms, benzylidene, p-xylylene, α,α,α',α'-tetramethyl-m-xylylene or cycloalkylidene, and T is —SO—, —SO$_2$—, —SO—E—SO—, —SO$_2$—E—SO$_2$—, —CO—, —CO—CO—, —CO—CH$_2$—CO—, —CO—E—CO—, —COO—E—OCO— or —CO—NG$_5$—E—NG$_5$—CO—, where E is alkylene of 2 to 12 carbon atoms, cycloalkylene of 5 to 12 carbon atoms, or alkylene interrupted or terminated by cyclohexylene of 8 to 12 carbon atoms;

G$_5$ is G$_3$ or hydrogen, and with the proviso that when T is —SO—, —SO$_2$—, —SO—E—SO— or —SO$_2$—E—SO$_2$—, E$_1$ is not hydrogen, straight or branched chain alkyl of 1 to 24 carbon atoms, cycloalkyl of 5 to 12 carbon atoms or phenylalkyl of 7 to 15 carbon atoms; or when E$_3$ is alkyl of 1 to 6 carbon atoms, E$_1$ is not hydrogen or phenyl, and the sum of E$_1$ plus E$_2$ is equal to or greater than 8; and when E$_3$ is alkyl of 8 to 18 carbon atoms or alkenyl of 2 to 24 carbon atoms, E$_1$ is not hydrogen, straight or branched chain of 1 to 24 carbon atoms, cycloalkyl of 5 to 12 carbon atoms or phenylalkyl of 7 to 15 carbon atoms; or when G$_2$ is cyano, —CO—G$_3$.—CONHG$_3$, —CON(G$_3$)$_2$ or —COOG$_3$, then E$_1$ is phenyl or phenylalkyl of 7 to 15 carbon atoms, or said phenyl or said phenylalkyl substituted on the phenyl ring by 1 to 4 alkyl of 1 to 4 carbon atoms; or when E$_1$ is hydrogen, E$_2$ is not methyl.

Preferably, the new benzotriazole is a compound of formula I

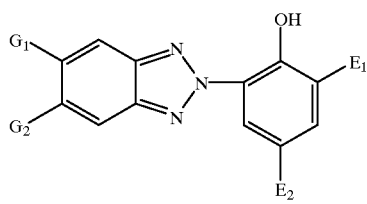

(I)

wherein

G$_1$ is hydrogen,

G$_2$ is cyano, CF$_3$—, fluoro, —CO—G$_3$ or E$_3$SO$_2$—,

G$_3$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, E$_1$ is phenylalkyl of 7 to 15 carbon atoms, phenyl, or said phenyl or said phenylalkyl substituted on the phenyl ring by 1 to 4 alkyl of 1 to 4 carbon atoms, E$_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or E$_2$ is said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where E$_4$ is straight or branched chain alkyl of 1 to 24 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof;

E$_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms; or is a compound of formula I wherein, G$_1$ is hydrogen, G$_2$ is CF$_3$—, fluoro or E$_3$SO$_2$—, E$_1$ is hydrogen or straight or branched alkyl of 4 to 24 carbon atoms, E$_2$ is as defined above, and E$_3$ is straight or branched chain alkyl of 1 to 7 carbon atoms, with the proviso that the sum of the carbon atoms in E$_1$ and E$_2$ is greater than or equal to 8 when G$_2$ is E$_3$SO$_2$.

Preferably, the benzotriazole is also a compound of formula IIIA

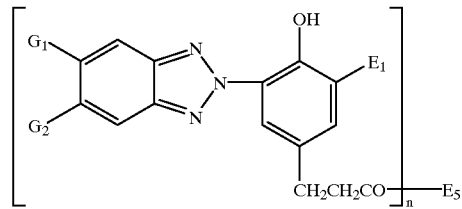

(IIIA)

wherein

G$_1$ is hydrogen,

G$_2$ is CF$_3$— or fluoro,

E$_1$ is hydrogen, straight or branched alkyl of 4 to 24 carbon atoms or phenylalkyl of 7 to 15 carbon atoms, E$_5$ is —OE$_6$ or —NE$_7$E$_8$, or E$_5$ is —X—(Z)$_p$—Y—E$_{15}$ wherein X is —O— or —N(E$_{16}$)—, Y is —O— or —N(E$_{17}$)—, Z is C$_2$–C$_{12}$-alkylene, C$_4$–C$_{12}$-alkylene interrupted by one to three nitrogen atoms, oxygen atoms or a mixture thereof, or is C$_3$–C$_{12}$-alkylene, butenylene, butynylene, cyclohexylene or phenylene, each substituted by a hydroxyl group, m is 0, 1, 2 or 3, p is 1, or p is also zero when X and Y are —N(E$_{16}$)— and —N(E$_{17}$)—, respectively, E$_{15}$ is a group —CO—C(E$_{18}$)=C(H)E$_{19}$ or, when Y is —N(E$_{17}$)—, forms together with E$_{17}$ a group —CO—CH=CH—CO—, wherein E$_{18}$ is hydrogen or methyl, and $E_{19}$ is hydrogen, methyl or —CO—X—$E_{20}$, wherein $E_{20}$ is hydrogen, $C_1$–$C_{12}$-alkyl or a group of the formula.

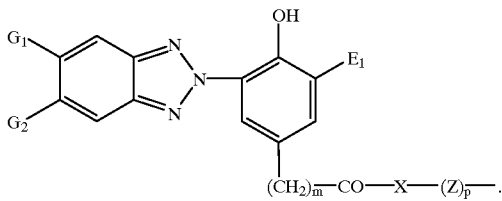

Preferably, the benzotriazole is also a compound of formula IV

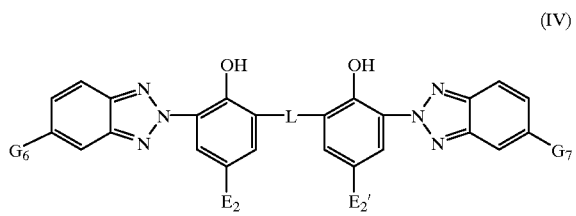

wherein $G_6$ is $CF_3$, $G_7$ is hydrogen or $CF_3$, $E_2$ and $E_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; and L is alkylene of 1 to 12 carbon atoms, alkylidene of 2 to 12 carbon atoms, benzylidene, p-xylylene, α,α,α',α'-tetramethyl-m-xylylene or cycloalkylidene.

Most preferably, the new benzotriazole is a compound of formula I

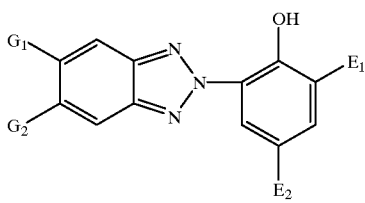

wherein $G_1$ is hydrogen, $G_2$ is $CF_3$—, $E_1$ is phenylalkyl of 7 to 15 carbon atoms, phenyl, or said phenyl or said phenylalkyl substituted on the phenyl ring by 1 to 4 alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is said alkyl of 1 to 24 carbon atoms or said alkenyl of 2 to 18 carbon atoms substituted by one or more —OH, —OCO$E_{11}$, —NH$_2$ or —NHCOE$_{11}$, or mixtures thereof; or said alkyl or said alkenyl interrupted by one or more —O— which can be unsubstituted or substituted by one or more —OH groups; or is a compound of formula I wherein, $G_6$ is hydrogen, $G_2$ is $CF_3$—, $E_1$ is hydrogen, straight or branched alkyl of 4 to 24 carbon atoms or phenylalkyl of 7 to 15 carbon atoms, and $E_2$ is as defined above.

Most preferably, the benzotriazole is also a compound of formula IIIA

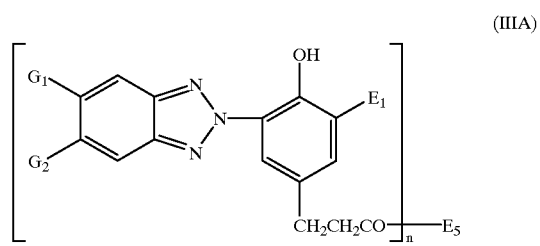

wherein $G_1$ is hydrogen, $G_2$ is $CF_3$—, $E_1$ is hydrogen, straight or branched alkyl of 4 to 24 carbon atoms or phenylalkyl of 7 to 15 carbon atoms, $E_5$ is —O$E_6$ or —N$E_7E_8$ where $E_6$ is hydrogen, straight or branched chain $C_1$–$C_{24}$alkyl which is unsubstituted or substituted by one or more OH groups, or —O$E_6$ is —(OCH$_2$CH$_2$)$_w$OH or —(OCH$_2$CH$_2$)$_w$O$E_{21}$ where w is 1 to 12 and $E_{21}$ is alkyl of 1 to 12 carbon atoms, and $E_7$ and $E_8$ are independently hydrogen, alkyl of 1 to 18 carbon atoms, straight or branched chain $C_3$–$C_{18}$alkyl which is interrupted by —O—, —S— or —N$E_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring.

Most preferably, the benzotriazole is also a compound of formula IV

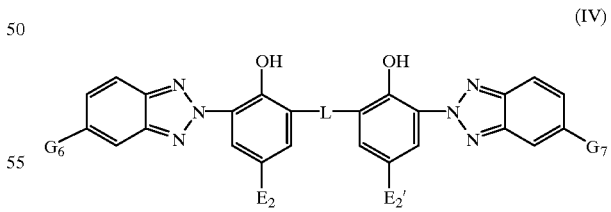

wherein $G_6$ is $CF_3$, $G_7$ is hydrogen or $CF_3$, $E_2$ and $E_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; and L is methylene.

Compounds which are especially preferred are:
(a) 5-trifluoromethyl-2-(2-hydroxy-3-α-cumyl-5-tert-octylphenyl)-2H-benzotriazole;
(b) 5-trifluoromethyl-2-(2-hydroxy-5-tert-octylphenyl)-2H-benzotriazole;
(c) 5-trifluoromethyl-2-(2-hydroxy-3,5-di-tert-octylphenyl)-2H-benzotriazole;
(d) 2,2'-methylene-bis[6-(5-trifluoromethyl-2H-benzotriazol-2-yl)-4-tert-octyl-phenol];
(e) methylene-2-[4-tert-octyl-6-(2H-benzotriazol-2-yl)phenol]2'-[4-tert-octyl-6-(5-trifluoromethyl-2H-benzotriazol-2-yl)phenol];
(f) 3-(5-trifluoromethyl-2H-benzotriazol-2-yl)-5-tert-butyl-4-hydroxyhydrocinnamic acid;
(g) methyl 3-(5-trifluoromethyl-2H-benzotriazol-2-yl)-5-tert-butyl4-hydroxyhydrocinnamate;
(h) isooctyl 3-(5-trifluoromethyl-2H-benzotriazol-2-yl)-5-tert-butyl-4-hydroxyhydrocinnamate;
(i) 5-trifluoromethyl-2-[2-hydroxy-5-(3-hydroxypropyl)phenyl]-2H-benzotriazole;
(j) 5-trifluoromethyl-2-[2-hydroxy-5-(3-acryloyloxypropyl)phenyl]-2H-benzotriazole;
(k) 5-trifluoromethyl-2-[2-hydroxy-5-(3-methacryloyloxypropyl)phenyl]-2H-benzotriazole;
(l) 5-trifluoromethyl-2-[2-hydroxy-5-(3-acrylylaminopropyl)phenyl]-2H-benzotriazole;
(m) 5-trifluoromethyl-2-[2-hydroxy-5-(3-methacrylylaminopropyl)phenyl]-2H-benzotriazole;
(n) 5-trifluoromethyl-2-(2-hydroxy-3-α-cumyl-5-tert-butylphenyl)-2H-benzotriazole;
(o) 5-trifluoromethyl-2-(2-hydroxy-3-α-cumyl-5-nonylphenyl)-2H-benzotriazole;
(p) 5-trifluoromethyl-2-[2-hydroxy-3-α-cumyl-5-(2-hydroxyethyl)phenyl]-2H-benzotriazole;
(q) 5-trifluoromethyl-2-[2-hydroxy-3-α-cumyl-5-(3-hydroxypropyl)phenyl]-2H-benzotriazole;
(r) 5-trifluoromethyl-2-(2-hydroxy-3,5-ditert-amylphenyl)-2H-benzotriazole;
(s) 5-trifluoromethyl-2-(2-hydroxy-3,5-ditert-butylphenyl)-2H-benzotriazole;
(t) 5-trifluoromethyl-2-(2-hydroxy-3-dodecyl-5-methylphenyl)-2H-benzotriazole;
(u) 5-trifluoromethyl-2-[2-hydroxy-3-tert-butyl-5-(3-hydroxypropyl)phenyl]-2H-benzotriazole;
(v) 5-trifluoromethyl-2-[2-hydroxy-3-tert-butyl-5-(2-hydroxyethyl)phenyl]-2H-benzotriazole;
(w) 5-trifluoromethyl-2-[2-hydroxy-5-(2-hydroxyethyl)phenyl]-2H-benzotriazole;
(x) 5-trifluoromethyl-2-(2-hydroxy-3,5-di-α-cumylphenyl)-2H-benzotriazole;
(y) 5-fluoro-2-(2-hydroxy-3,5-di-α-cumylphenyl)-2H-benzotriazole;
(z) 5-butylsulfonyl-2-(2-hydroxy-3,5-di-α-cumylphenyl)-2H-benzotriazole;
(aa) 5-butylsulfonyl-2-(2-hydroxy-3,5-di-tert-butylphenyl)-2H-benzotriazole; and
(bb) 5-butylsulfonyl-2-(2-hydroxy-3,5-di-tert-octylphenyl)-2H-benzotriazole.

Examples of these various radicals are as follow:

When any of $E_1$ to $E_{21}$ is alkyl, such groups are, for example, methyl, ethyl, isopropyl, n-butyl, isobutyl, sec-butyl, tert-butyl, tert-amyl, 2-ethylhexyl, tert-octyl, lauryl, tert-dodecyl, tridecyl, n-hexadecyl, n-octadecyl and eicosyl; when any of said radicals is alkenyl, such groups are, for example, allyl or oleyl; when any of said radicals is cycloalkyl, such groups are, for example, cyclopentyl, cyclohexyl, cycloheptyl, cyclooctyl and cyclododecyl; when any of said radicals are phenylalkyl, such groups are, for example, benzyl, phenethyl, α-methylbenzyl and α,α-dimethylbenzyl; and when any of said radicals is aryl, they are, for example, phenyl, naphthyl, or when substituted by alkyl are, for example, tolyl and xylyl. When $E_6$ is alkyl substituted by one or more —O— groups and/or substituted by one or more —OH, the —$OE_6$ moiety can be —$(OCH_2CH_2)_w$OH or —$(OCH_2CH_2)_w OE_{21}$ where w is 1 to 12 and $E_{21}$ is alkyl of 1 to 12 carbon atoms, for example.

When E is alkylene, it is, for example, ethylene, tetramethylene, hexamethylene, 2-methyl-1,4-tetramethylene, hexamethylene, octamethylene, decamethylene and dodecamethylene; when E is cycloalkylene, it is, for example, cyclopentylene, cyclohexylene, cycloheptylene, cyclooctylene and cyclododecylene; and when E is alkylene interrupted or terminated by cyclohexylene, it is, for example, the saturated diyl radical derived from limonene, herein called dihydrolimonenediyl.

When E is alkylene, it is, for example, ethylene, tetramethylene, hexamethylene, 2-methyl-1,4-tetramethylene, hexamethylene, octamethylene, decamethylene and dodecamethylene; when E is cycloalkylene, it is, for example, cyclopentylene, cyclohexylene, cycloheptylene, cyclooctylene and cyclododecylene; and when E is alkylene interrupted or terminated by cyclohexylene, it is, for example, the saturated diyl radical derived from limonene, herein called dihydrolimonenediyl.

When the instant compounds contain a free carboxyl moiety where $E_2$ is —$CH_2CH_2COOE_6$ where $E_6$ is hydrogen, the alkali metal or amine salts of said acids are also contemplated as part of this invention allowing such UV absorbers to be used in aqueous systems due to the enhanced water solubility of such instant compounds.

$E_6$, $E_7$ and $E_8$ can be the following $C_3$–$C_{18}$alkyl radicals which are interrupted by —O—, —S—, or —$NE_{11}$— and can be substituted by OH: methoxyethyl, ethoxyethyl, butoxyethyl, butoxypropyl, methylthioethyl, $CH_3OCH_2CH_2OCH_2CH_2$—, $CH_3CH_2OCH_2CH_2OCH_2CH_2$—, $C_4H_9OCH_2CH_2OCH_2CH_2$—, ethylthiopropyl, octylthiopropyl, dodecyloxypropyl, 2-hydroxyethyl, 2-hydroxypropyl, 4-hydroxybutyl, 6-hydroxyhexyl, —$CH_2CH_2$—NH—$C_4H_9$, —$CH_2CH_2CH_2$NH—$C_8H_{17}$ and —$CH_2CH_2CH_2$—$N(CH_3)$—$CH_2CH(C_2H_5)C_4H_9$, $E_6$, $E_7$, $E_8$, $E_{11}$ and $E_{12}$ can be the following $C_5$–$C_{12}$cycloallyl radicals: cyclopentyl, cyclohexyl, cycloheptyl, cyclooctyl or cyclodecyl. In the case of $E_6$, the radical can also be substituted by —OH.

$E_7$, $E_8$ and $E_{11}$ can be the following alkenyl radicals: allyl, methallyl, 2-n-hexenyl or 4-n-octenyl.

When $E_6$ is alkenyl, it can have the same meaning as $E_7$, $E_8$ and $E_{11}$ as alkenyl radicals, but it can also be —CH=$CH_2$, n-undec-10-enyl or n-octadec-9-enyl, and it is also possible for the radical $E_6$ to be substituted by —OH.

$E_7$ and $E_8$ can be the following $C_7$–$C_{15}$aralkyl radicals: benzyl, α-phenethyl, 2-phenethyl or 4-tert-butylbenzyl.

When $E_{11}$, $E_{13}$ or $E_{12}$ are aralkyl, they can, independently of one another, have the same meaning as $E_7$ or $E_8$.

Independently of one another, $E_7$, $E_8$ and $E_{11}$ can be the following $C_6$–$C_{14}$ aryl radicals: phenyl, α-naphthyl or β-naphthyl.

When $E_7$ and $E_8$ are $C_1$–$C_3$ hydroxyalkyl, they can be the following radicals: hydroxymethyl, 2-hydroxyethyl or 2-hydroxypropyl.

As $C_2$–$C_8$ alkylene, $E_9$ and $E_{14}$ can be the following radicals: ethylene, propylene, butylene, hexylene or octylene.

As alkylene, $E_{10}$ can be the same radicals, but can, in addition, also be higher-molecular groups such as decylene or dodecylene.

When $E_9$ is a $C_4$–$C_8$ alkenylene radical, the following is an example of a suitable group: butenylene.

In the case of $E_9$ and $E_{14}$, suitable straight or branched chain $C_4$–$C_{10}$ alkylene groups which are interrupted by —O— are the following groups: —$CH_2CH_2OCH_2CH_2$—, —$CH(CH_3)$—$CH_2$—O—$CH_2$—$CH(CH_3)$— $CH_2CH_2OCH_2CH_2OCH_2CH_2$— and —$CH_2CH_2OCH_2CH_2OCH_2CH_2OCH_2CH_2$—.

When $E_{14}$ is a cycloalkylene radical, the following groups are embraced: 1,3-cyclohexylene and 1,4-cyclohexylene.

When $E_{14}$ is arylene, this can be, specifically, the following groups: 1,3-phenylene or 1,4-phenylene.

As $C_2$–$C_{12}$-alkylene, Z is a straight or branched chain. It is for example: ethylene, propylene, tetramethylene, hexamethylene, octamethylene, dodecamethylene, 1,1-ethylidene, 2,2-propylidene, 2,2-amylidene or 2-ethylhexamethylene. $C_2$–$C_6$-alkylene groups are preferred.

When Z is $C_4$–$C_{12}$-alkylene which is interrupted by oxygen, it is for example: —$CH_2$—$CH_2$13 O—$CH$—$_2$—$CH_2$—, —$CH_2$—$CH_2$—O—$CH_2$—$CH_2$—$CH_2$, $CH_2$—$CH_2$—O—$CH_2$—$CH_2$—O—$CH_2$—$CH_2$ or —$CH_2$—$CH_2$—O—$CH_2$—$CH_2$—O—$CH_2$—$CH_2$—O—$CH_2$—$CH_2$—, and, when alkylene is interrupted by nitrogen, a group —$N(E_{16})$— is meant, where $E_{16}$ is as defined in the foregoing, for example —$CH_2$—$CH_2$—NH—$CH_2$—$CH_2$—$CH_2$—$CH_2$, —$CH_2$—$CH_2$—$CH_2$—NH—$(CH_2)_8$— or —$CH_2CH_2$—$CH_2$—$N(CH_3$—$CH_2$—$CH(C_2H_5)(CH_2)_4$—.

As $C_3$–$C_{12}$-alkylene substituted by a hydroxyl group, Z is 2-hydroxytetramethylene, 2-hydroxyhexamethylene and, in particular, 2-hydroxytrimethylene.

As cyclohexylene, Z is for example 1,4cyclohexylene and, in particular, 1,2-cyclohexylene.

As phenylene, Z is for example m-phenylene or p-phenylene.

m can be zero, 1, 2 or 3, but it is preferably 2.

p is preferably 1, but can also be zero if both X and Y are bound by way of nitrogen.

As $C_1$–$C_8$-alkyl, $E_1$ is for example: methyl, ethyl, n-propyl, isopropyl, n-butyl, sec-butyl, tert-butyl, n-pentyl, tert-amyl, n-nexyl, n-heptyl, n-octyl, 2-ethylhexyl or tert-octyl. Tert-butyl is preferred.

As $C_1$–$C_{12}$-alkyl, $E_{16}$, $E_{17}$ and $E_{20}$ can have the same meaning as that given in the foregoing for $R_1$, and can additionally be straight or branched-chain nonyl, decyl, undecyl, or dodecyl.

When $E_{16}$ and $E_{17}$ are alkyl interrupted by oxygen atoms, the examples which apply are the same as those described in the foregoing for Z.

Examples for $E_{16}$ and $E_{17}$ as aralkyl are: benzyl, α-methylbenzyl, 1-phenylethyl, α,α-dimethylbenzyl or 1-phenylpropyl.

If Z is ethylene, $E_{16}$ and $E_{17}$ together can likewise form ethylene, which is equivalent to a bridging over by way of a piperazine group.

When Y is a group —$N(E_{17})$—, $E_{15}$ and $E_{17}$ together make up a group —CO—CH=CH—CO—, and thus form the substituent

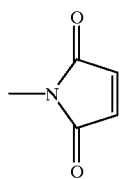

on the group —X—$(Z)_p$—.

The preferred meaning of $E_{15}$ is, however, —CO—$C(E_{18})$=$CHE_{14}$, $E_{18}$ and $E_{19}$ are preferably methyl and especially hydrogen.

$E_2$ is —$CH_2$—$CH_2$—O—CO—$C(G)$=$CH_2$ and G is hydrogen or methyl.

The instant invention also pertains to a composition stabilized against thermal, oxidative or light-induced degradation which comprises, (a) an organic material subject to thermal, oxidative or light-induced degradation, and
(b) an effective stabilizing amount of a compound of formula I, II, III or IV.

Preferably, the organic material is a natural, semi-synthetic or synthetic polymer, especially a thermoplastic polymer.

Most preferably, the polymer is a polyolefin or polycarbonate, especially polyethylene or polypropylene; most especially polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalene-dicarboxylate), or other blends or copolymers such as poly(ethylene/1,4-cyclohexylene-dimethylene terephthalate) PETG or an ionomer as described on page 29.

In another preferred embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

Most preferably, the resin is a thermoset acrylic melamine resin or an acrylic urethane resin.

In yet another preferred embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula I, II, III or IV can be incorporated into the carder material as early as the production of the latter, in the production of paper, for example, being added to the paper pulp. A second method of application is to spray the carder material with an aqueous solution of compounds of formula I, II, III or IV or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together, the solid components, for example, fillers and other additives already described, are dispersed in this aqueous medium; and dispersion is advantageously carried out by means of devices, for example, ultrasonic systems, turbine stirrers, homogenizers, colloid mills, bead mills, sand mills, high-speed stirrers and the like. The compounds of formula I, II, III or IV can be easily incorporated into the coating composition.

The recording material according to this invention preferably contains 1 to 5000 mg/m$^2$, in particular 50–1200 mg/m$^2$, of a compound of formula I.

As already mentioned, the recording materials according to the invention embrace a wide field. The compounds of formula I, II, III or IV can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula I, II, III or IV act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are preferably used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula I, II, III or IV can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and pen-plotters. Of the above, recording materials for dye diffusion transfer printing are preferred, for example, as described in EP-A 507,734.

The instant compounds can also be employed in inks, preferably for ink jet printing, for example, as described in U.S. Pat. No. 5,098,477 which is incorporated herein by reference.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

Preferred compounds are those in which one of X and Y is —O—; and particularly those in which both X and Y are —O—.

In general polymers which can be stabilized include
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/-isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4- dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%. However, some high performance films or in UV absorbing layers of laminates such as those produced by coextrusion may contain from 5–15% by weight of the instant compounds. Concentrations of 5–10% by weight are typical in certain coextrusion applications.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5di-tert-butyl-hydroquinone
2,5di-tert-amyl-hydroquinone
2,6diphenyl-4-octadecyloxyphenol
1.3. Hydroxylated thiodiphenyl ethers, for example,
2,2'-thio-bis-(6-tert-butyl4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4isobutylphenol)
4,4'-methylene-bis-(2,6di-tert-butylphenol)
4,4'-methylene-bis-(6-tert-butyl-2-methylphenol)
1,1-bis-(5-tert-butyl4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene di-[2-(3'-tert-butyl-2'-hydroxy-5'-methyl-benzyl)-6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl) isocyanurate
3,5-di-tert-butyl-4-hydroxybenzyl-phosphoric acid diocta-decyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-,3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6tetramethylpiperidyl)sebacate, bis-(1,2,2,6,6-pentamethylpiperidyl)sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl)sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)4-(2,4-dihydroxyphenyl)-s-triazine; 2,4-bis(2,4-dihydroxyphenyl)-6-(4-chlorophenyl)-s-triazine; 2,4-bis [2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4dimethylphenyl)-s-triazine.

3. Metal deactivators, for example, N,N'-diphenyloxalic acid diamide, N-salicylal-N'-salicyloyl-hydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert-butylphenyl) phosphite, di-isodecyl-pentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl)4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecyl-hydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. Nos. 4,325,863, 4,338,244 or 5,175,312, or 3-[4-(2-acetoxyethoxy)phenyl]-5,7-di-tert-butyl-benzo-furan-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl)-benzofuran-2-one, 3-(4-acetoxy-3,5-dimethylphenyl)-5,7-di-tert-butyl-benzofuran-2-one, 3-(3,5-di-methyl-4-pivaloyloxyphenyl)-5,7-di-tert-butyl-benzofuran-2-one.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also particularly preferred are benzofuran-2-ones, such as described, for example, in U.S. Pat. Nos. 4,325,863, 4,338,244 or 5,175, 312.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6tris(3,5-di-tert-butyl-4-hydroxy-benzyl) benzene, 3,6 -dioxaoctamethylene bis(3-methyl-5-tert-butyl-4-hydroxyhydrocinnamate), 2,6di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl)1,2,3,4-butanetetracarboxylate, tetrakis(1,2,2,6,6-pentamethylpiperidin-4-yl)1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N",N'"-tetrakis[(4,6-bis(butyl-1,2,2,6,6-pentamethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl]1,2,3,4-butanetetracarboxylate, mixed [1,2,2,6,6-pentamethylpiperidin4-yl/β,β,β',β'-tetramethyl-3,9-(2,4,8,10-tetraoxaspiro[5.5]-undecane)diethyl]1,2,3,4-butanetetracarboxylate, octamethylene bis(2,2,6,6-tetramethyl-piperidin-4-carboxylate), 4,4'-ethylenebis(2,2,6,6-tetramethylpiperazin-3-one), N-2,2,6,6-tetramethyl-piperidin-4-yl-n-dodecylsuccinimide, N-1,2,2,6,6-pentamethyl-piperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl)sebacate, di-(1-cyclohexyloxy-2,2,6,6-tetra-methylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N",N'"-tetrakis[(4,6-bis(butyl-(1,2,2,6,6-pentamethylpiperidin-4-yl)amino)-s-triazine-2-yl]-1,10-diamino-4,7-diazadecane.di-(1-octyloxy-2,2,6,6-tetramethylpiperidin-4-yl)sebacate, di-(1-cyclohexyloxy-2,2,6,6-tetramethylpiperidin4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The instant composition can additionally contain another UV absorber selected from the group consisting of the benzotriazoles, s-triazines, the oxanilides, the hydroxybenzophenones, benzoates and the α-cyanoacrylates.

Particularly, the instant composition may additionally contain an effective stabilizing amount of at least one other 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;
2-[2-hydroxy-3,5-di(α,α-dimethylbenzyl)phenyl]-2H-benzotriazole;
2-[2-hydroxy-3-(α,α-dimethylbenzyl)-5-tert-octylphenyl]-2H-benzotriazole;
2-{2-hydroxy-3-tert-butyl-5-[2-(omega-hydroxy-octa (ethyleneoxy)carbonyl)ethyl]-phenyl}-2H-benzotriazole;
5-chloro-2-(2-hydroxy-3,5-di-tert-butylphenyl)-2H-benzotriazole;
5-chloro-2-(2-hydroxy-3-tert-butyl-5-methylphenyl)-2H-benzotriazole;
2-(2-hydroxy-5-tert-octylphenyl)-2H-benzotriazole; and
2-(2-hydroxy-3-tert-butyl-5-[2-(octyloxy)carbonyl)ethyl] phenyl}-2H-benzotriazole.

Preferably, the other tris-aryl-s-triazine is selected from the group consisting of
2,4-bis(2,4-dimethylphenyl)-6-(2-hydroxy-4-octyloxyphenyl)-s-triazine;
2,4-diphenyl-6-(2-hydroxy-4-hexyloxyphenyl)-s-triazine;
2,4-bis(2,4-dimethylphenyl)-6-[2-hydroxy-4-(3-do-/tri-decyloxy-2-hydroxypropoxy)-phenyl]-s-triazine; and
2-{(2-hydroxyethylamino)-4,6-bis[N-butyl-N-(1-cyclohexyloxy-2,2,6,6-tetramethyl-piperidin4-yl)amino]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional cross-linkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be especially useful in other applications where their enhanced durability is required such as in solar films and the like.

The following examples are for illustrative purposes only and are not to be construed to limit the scope of the instant invention in any manner whatsoever.

EXAMPLE 1

5-Trifluoromethyl-2-(2-hydroxy-3-α-cumyl-5-tert-octylphenyl)-2H-benzotriazole a. Diazotization of 4-amino-3-nitro-benzotrifluoride To a 500 ml 3-necked flask, equipped with a mechanical stirrer, are added 41.2 g of 4-amino-3-nitro-benzotrifluoride, 52 ml of concentrated hydrochloride acid and 100 ml of distilled water. The stirred solution is cooled to 5° C. and 17.3 g of sodium nitrite dissolved in 50 ml of water are added. The solution is stirred at 0 to 5° C. for two hours, then filtered and stored at −10° C.

b. Monoazo adduct

To a 1000 ml flask, fitted with a mechanical stirrer, are added 40 g of sodium hydroxide dissolved in 200 ml of methanol and 32.4 g of 2-α-cumyl-4-tert-octylphenol in 50 ml of xylene. The solution is cooled to 5° C. and the diazo solution of 4-amino-nitro-benzotrifluoride prepared in part a. is added at 0 to 5° C. over a two-hour period. Then 100 ml of xylene are added and the organic layer is washed with water, aqueous hydrochloride acid, water, aqueous sodium bicarbonate solution and finally water. The solvent is removed under reduced pressure and the residue is purified by chromatography (silica gel, heptane:ethyl acetate 95:5) to yield 42.1 g of the adduct product as a dark red paste.

c. Reduction of the monoazo adduct

A 1000 ml flask is charged with 20 g of sodium hydroxide, 40 ml of water, 42.1 g of the monoazo adduct prepared in part b. and 400 ml of ethanol. The mixture is warmed to 80° C. and 27 g of formamidine sulfinic acid is added in portions with stirring. After 1.5 hours, the solution is cooled to room temperature and 100 ml of water are added. The pH is adjusted to pH 7 with concentrated hydrochloric acid. The ethanol is removed under vacuum and the water layer is extracted with methylene chloride. The solvent is then evaporated in vacuo and the residue is purified by chromatography (silica gel, heptane:tolunen 9:1) and crystallized from ethanol. The title compound is obtained in a yield of 5.6 g as a pale yellow solid melting at 119–121° C.

EXAMPLE 2

5-Fluoro-2-(2-hydroxy-3-α-cumyl-5-tert-octylphenyl)-2H-benzotriazole

The title compound is prepared according to the general procedure of Example 1 using 31.2 g of 4-fluoro-2-nitroaniline. In part c of the procedure, an additional 9 g of formamidine sulfinic acid is required to complete the reduction. Purification of the crude product on silica gel (heptane:toluene, 1:1) yields 4.5 g of the title compound as a off-white solid. Further purification by recrystallization from acetonitrile:toluene provides 1.1 g of the tide compound melting at 93–96° C.

EXAMPLE 3

5-Chloro-2-(2-hydroxy-3-α-cumyl-5-tert-octylphenyl)-2H-benzotriazole

The general procedure of Example 1 parts a and b is followed to prepare the monoazo intermediate of making the tide compound from 339.3 g of 4-chloro-2-nitro-aniline. The crude product is purified by recrystallization from methanol to yield 70.9 g of deep red monoazo adduct.

Reduction of the Monoazo Adduct

A mixture of 11.8 g of sodium hydroxide and 138 g of 2-butanol is heated to 95° C. A solution of 60.1 g of the above monoazo adduct and 1.3 g of 2,3-dichloro-1,4naphtho-quinone in 90 g of 2-butanol is added over a 90 minute period with stirring. The reaction mixture is heated to remove the 2-butanone byproduct with additional 2-butanol added to replace the distillate. The reaction mixture is cooled to 85° C., washed with 2.5 N sulfuric acid and brine and then concentrated. The residue is recrystallized from methanol:xylene to yield 45.6 g of the title compound as a light yellow solid melting at 104–105° C.

EXAMPLE 4

5-Phenylthio-2-(2-hydroxy-3-α-cumyl-5-tert-octylphenyl)-2H-benzotriazole

To a stirred mixture of 75 g of 5-chloro-2-(2-hydroxy-3-α-cumyl-5-tert-octyl-phenyl)-2H-benzotriazole and 105 g of N-methylpyrrolidone heated at 90° C. is added first 44.3 g of 45% aqueous potassium hydroxide solution over a 15-minute period then 20.4 g of thiophenol over another 15 minutes. The reaction mixture is then heated at 170–175° C. for four hours with water being removed by distillation. After cooling to 100° C., xylene and water are added and the resultant mixture is made acidic with 15% aqueous hydrogen chloride solution. The organic layer is separated and washed with water and then concentrated. The crude product residue is recrystallized from methanol to yield 82 g of the title compound as a pale yellow solid melting at 124–125° C.

EXAMPLE 5

5-Benzenesulfonyl-2-(2-hydroxy-3-α-cumyl-5-tert-octylphenyl)-2H-benzotriazole

A 1000 mL flask is charged with 75.2 g of 5-phenylthio-2-(2-hydroxy-3-α-cumyl-5-tert-octylphenyl)-2H-benzotriazole, prepared in Example 4, 102 g of xylene, 0.9 g of sodium tungstate dihydrate and 18.4 g of formic acid. The mixture is heated to 50° C. To this stirred mixture is slowly added 36.3 g of 50% hydrogen peroxide so that the temperature does not exceed 85° C. Additional xylene and water are then added. The organic layer is separated, washed with aqueous sodium sulfite, then twice with water and concentrated. The crude product residue is recrystallized from methanol to yield 75.2 g of the title compound as a light yellow solid melting at 170–171° C.

EXAMPLE 6

5-Nonylthio-2-(2-hydroxy-3-α-cumyl-5-tert-octylphenyl)-2H-benzotriazole

Using the procedure of Example 4 with 30 g of 5-chloro-2-(2-hydroxy-3-α-cumyl-5-tert-octylphenyl)-2H-benzotriazole and 17.6 g of nonyl mercaptan, the title compound is prepared.

EXAMPLE 7

5-Nonylsulfonyl-2-(2-hydroxy-3-α-cumyl-5-tert-octylphenyl)-2H-benzotriazole

5-Nonylthio-2-(2-hydroxy-3-α-cumyl-5-tert-octylphenyl)-2H-benzotriazole, prepared in Example 6, is oxidized to the sulfone without purification of the thio intermediate using 8.7 g of formic acid, 0.7 g of sodium tungstate dihydrate and 17.6 g of 50% hydrogen peroxide to yield the title compound as a yellow resin exhibiting a molecular ion of m/e 631. This process is described in detail in copending application Serial No. XXXXXX.

EXAMPLE 8

5-Chloro-2-(2-hydroxy-3-phenyl-5-tert-octylphenyl)-2H-benzotriazole

The general procedure of Example 1 parts a and b are used to prepare the monoazo intermediate for the title compound from 4-chloro-2-nitroaniline and 2-phenyl-4-tert-octylphenol. The crude product is purified by recrystallization from methanol to yield a deep red monoazo adduct.

The title compound is prepared according to the reduction procedure of Example 3 from 65 g of the monoazo adduct prepared above, 19.9 g of sodium hydroxide and 2.4 g of 2,3-dichloro-1,4-naphthoquinone. The crude product is purified by chromatography on silica gel (hexane:ethyl acetate, 5:1) yielding a fraction which is predominantly the title compound exhibiting a molecular ion of m/e 433.

EXAMPLE 9

5-Phenylthio-2-(2-hydroxy-3-phenyl-5-tert-octylphenyl)-2H-benzotriazole

The title compound is prepared according to the procedure of Example 4 from 20 g of the compound of Example 8, 20.4 g of 45% aqueous potassium hydroxide, 10.3 g of thiophenol and 100 g of N-methylpyrrolidone. The title compound is an oil purified by chromatography on silica gel using toluene as eluent.

EXAMPLE 10

5-Benzenesulfonyl-2-(2-hydroxy-3-phenyl-5-tert-octylphenyl)-2H-benzotriazole

The title compound is prepared according to the procedure of Example 5 from 20 g of the thio compound of Example 9, 6.4 g of formic acid, 15.0 g of 50% hydrogen peroxide and 0.6 g of sodium tungstate dihydrate. Recrystallization of 2.5 g of crude material from xylene/methanol yields 2.0 g of the purified title compound as a light yellow powder melting at 204–206° C.

EXAMPLE 11

Mixture of 5-Chloro-2-(2-hydroxy-3,5-dialkylphenyl)-2H-benzotriazole (alkyl being independently $C_4$, $C_8$, $C_{12}$ and $C_{16}$)

A mixture of 65.4 g of 5-chloro-2-(2-hydroxy-3,5-dialkylphenyl)-2H-benzotriazole, 45 mL of dodecene and 13 mL of methane sulfonic acid is heated to 170° C. under nitrogen. An additional 135 mL of dodecene is added over a 4.5 hour period. The reaction mixture is allowed to cool to 100° C. and then quenched with 400 g of crushed ice and extracted thrice with ethyl acetate. The organic layers are combined, washed with water, aqueous sodium bicarbonate, water again and brine, dried over anhydrous magnesium sulfate and finally concentrated. The polymeric residue is removed by bulb to bulb distillation under vacuum at 0.2 mm and up to 210° C. Unreacted starting material is then removed by distillation (at 0.01 mm, 160° C.) to give 45 g of the title mixture as a yellow oil.

EXAMPLE 12

Mixture of 5-Phenylthio-2-(2-hydroxy-3,5-dialkylphenyl)-2H-benzotriazole (alkyl being independently $C_4$, $C_8$, $C_{12}$ and $C_{16}$)

The title mixture is prepared according to the procedure of Example 4 using 40 g the mixture of Example 11, 11.2 g of potassium hydroxide and 12.3 mL of thiophenol.

EXAMPLE 13

Mixture of 5-Benzenesulfonyl-2-(2-hydroxy-3,5-dialkylphenyl)-2H-benzotriazole (alkyl being independently $C_4$, $C_8$, $C_{12}$ and $C_{16}$)

A mixture of the crude product of Example 12, 350 mL of isopropanol, 14.7 mL of formic acid and 1.8 mL of concentrated sulfuric acid are heated to reflux and 30 mL of 50% hydrogen peroxide is added dropwise over a two-hour period. After an additional three hours at reflux, the reaction mixture is cooled and 10% aqueous sodium sulfite and aqueous sodium bicarbonate are added. The isopropanol is evaporated and the residue is extracted with methylene chloride. The organic layer is washed with water and then dried over anhydrous magnesium sulfate. The solution is concentrated to leave 45 g of crude product as a viscous prange oil. Some 30 g of this crude product is purified by chromatography on silica gel (heptane:ethyl acetate, 4:1) to yield 28.9 g of the title mixture as a yellow oil.

EXAMPLE 14

5-Diphenylphosphinyl-2-(2-hydroxy-3,5-tert-butylphenyl)-2H-benzotriazole

To a flame-dried 500 mL three-necked round-bottomed flask equipped with a condenser, magnetic stirrer and thermometer are charged 100 mL of dimethyl sulfoxide, 7.41 g (0.066 mol) of potassium tert-butoxide and 11.17 g (0.060 mol) of diphenyl-phosphine via a syringe. A slurry of 10.56 g (0.030 mol) of 5-chloro-2-(2-hydroxy-3,5-di-tert-butylphenyl)-2H-benzotriazole in 50 mL of dimethyl sulfoxide is added all at once to the red mixture. The resultant brown solution is stirred at 135° C. for 3.5 hours and then cooled to room temperature. The mixture is quenched with a portion of saturated ammonium chloride solution and ethyl acetate is then added. The organic layer is separated and washed thrice with water, once with brine and then dried over anhydrous magnesium sulfate. To the solution is added 50% hydrogen peroxide resulting in an exotherm. The mixture is allowed to sit for 30 minutes, then washed once with 10% sodium metabisulfite solution thrice with saturated sodium bicarbonate solution once with brine and finally dried over anhydrous magnesium sulfate. The mixture is filtered with a plug of silica gel and the solvent is removed under reduced pressure to yield 8.0 g of a crude yellow solid. The crude product is treated with medium pressure chromatography using heptane:ethyl acetate, 1:1 to afford 4.2 g (27% yield) of the title compound as a yellow solid melting at 98–100° C.

EXAMPLE 15

5-Diphenylphosphinyl-2-(2-hydroxy-3-α-cumyl-5-tert-octylphenyl)-2H-benzotriazole Following the procedure of Example 14, the title compound is prepared when 5-chloro-2-(2-hydroxy-3-α-cumyl-5-tert-octylphenyl)-2H-benzotriazole is used as the starting benzotriazole intermediate.

EXAMPLES 16–26

Following the general procedure of Example 1, the following additional 2H-benzotriazoles of formula I are prepared.

| Example | $G_2$ | $E_1$ | $E_2$ |
| --- | --- | --- | --- |
| 16 | $CF_3$ | phenyl | tert-octyl |
| 17 | $CF_3$ | α-cumyl | tert-butyl |
| 18 | CN | α-cumyl | tert-octyl |
| 19 | CN | α-cumyl | nonyl |
| 20 | CN | α-cumyl | tert-butyl |
| 21 | $COOCH_3$ | α-cumyl | dodecyl |
| 22 | F | phenyl | tert-octyl |
| 23 | $CF_3$ | α-cumyl | nonyl |
| 24 | $CF_3$ | α-cumyl | dodecyl |
| 25 | $CON(Bu)_2$ | α-cumyl | tert-octyl |
| 26 | $COOCH_3$ | phenyl | tert-octyl |

EXAMPLE 27

5-Octylthio-2-(2-hydroxy-3-α-cumyl-5-tert-octylphenyl)-2H-benzotriazole

Using the procedure of Example 6 with 5-chloro-2-(2-hydroxy-3-α-cumyl-5-tert-octylphenyl)-2H-benzotriazole and octyl mercaptan, the title compound is prepared.

EXAMPLE 28

5-Octylsulfonyl-2-(2-hydroxy-3-α-cumyl-5-tert-octylphenyl)-2H-benzotriazole

5-Octylthio-2-(2-hydroxy-3-α-cumyl-5-tert-octylphenyl)-2H-benzotriazole, prepared in Example 27, is oxidized to the sulfone without purification of the thio intermediate using the general method of Example 7. A yellow resinous liquid is obtained whose structure is consistent as measured by $^1$HNMR.

EXAMPLE 29

5-Carbomethoxy-2-(2-hydroxy-3-α-cumyl-5-tert-octylphenyl)-2H-benzotriazole a. Esterification of 4-amino-3-nitrobenzoic Acid To a 2 L 3-necked flask fitted with a mechanical stirrer are added 700 mL of methanol, 20 g of xylene, 14 g concentrated sulfuric acid and 100 g of 4-amino-3-nitrobenzoic acid. The solution is heated to reflux for 33 hours. The mixture is cooled to 35° C. and neutralized to pH 7.8. Water (1 L) is added, the solid collected and washed with 500 ml to give after drying overnight 100.9 g of methyl 4-amino-3-nitrobenzoate.

b. Diazotization of methyl 4-amino-3-nitrobenzoate

To a 1 L 3-necked flask fitted with a mechanical stirrer is added 177 g of 96% sulfuric acid and then slowly over 90 minutes 11 g of sodium nitrite. The mixture is warmed to 30° C. to initiate the reaction. The temperature is kept below 70° C. The mixture is then cooled to 15° C. and 30 g of methyl 4-amino-3-nitrobenzoate is added over two hours keeping the temperature between 15–20° C. The mixture is cooled to 0° C. and 200 g of ice is added to make the solution suitable for the coupling reaction to form a monoazo compound.

c. Monoazo adduct

To a 2 L 3-necked flask fitted with a mechanical stirrer and addition funnel are added 52 g of 2-α-cumyl-4-tert-octylphenol, 20 g of water, 315 g of methanol, 7 g of xylene and 150 g of sodium hydroxide. The mixture is cooled to −5° C. and the diazonium salt solution prepared is step b. is added over a two hour period with cooling to keep the temperature below 3° C. After the diazonium salt solution is added, the pH is adjusted to 6.5–7.0. The mixture is poured into 500 mL of xylene and washed thrice with 500 mL of water at 60° C. The xylene is removed by distillation to give 186 g of the monoazo adduct containing residual xylene.

d. Reduction of the monoazo adduct

To a 500 mL flask fitted with a mechanical stirrer is added the 186 g of monoadduct prepared in step c., 125 g of 2-butanol and 1.7 g of 2,3-di-chloro-1,4-naphthoquinone. The mixture is heated to 90° C. and the resulting solution is then charged to the addition funnel on a separate flask. In said second flask are added 175 g of 2-butanol and 18.6 g of sodium hydroxide. The flask is heated to 95° C. and the monoazo solution is added over two hours while distilling off methyl ethyl ketone and 2-butanol. 2-Butanol (100 g) is added and an azeotrope is distilled off. The mixture is then cooled and 300 g of xylene and 200 mL of water are added. The pH is adjusted to 7–7.5 with 20% sulfuric acid. At 60° C., the aqueous phase is separated and the organic phase washed twice with 200 mL of water. The xylene is removed by distillation and the residue formed is crystallized from methanol to give 8.8 g of the title compound melting at 141–143° C.

EXAMPLE 30

5-[N,N-Di-n-butylcarbamoyl-2-(2-hydroxy-3-α-cumyl-5-tert-octyl)phenyl]-2H-benzotriazole a. Saponification of 5-Carbomethoxy-2-(2-hydroxy-3-α-cumyl-5-tert-octylphenyl)-2H-benzotriazole To a 250 mL 3-necked flask equipped with a mechanical stirrer, thermometer, condenser and nitrogen inlet is added 1.8 g of potassium hydroxide and 40 mL of methanol. The mixture is warmed to 40° C. to dissolve the potassium hydroxide. To this solution is added 2.7 g of 5-carbomethoxy-2-(2-hydroxy-3-α-cumyl-5-tert-octylphenyl)-2H -benzotriazole, prepared in Example 36, in 40 mL of methanol. The reaction mixture is refluxed for six hours. The mixture is then cooled and acidified with hydrochloric acid. Ether and ethyl acetate are added, and the organic layer is separated and dried over anhydrous sodium sulfate. After vacuum stripping of the solvent, 2.5 g of 5-carboxy-2-(2-hydroxy-3-α-cumyl-5-tert-octylphenyl)-2H-benzotriazole is isolated.

b. 5-Chlorocarbonyl-2-(2-hydroxy-3-α-cumyl-5-tert-octylphenyl)-2H-benzotriazole

The 2.5 g of 5-carboxy-2-(2-hydroxy-3-α-cumyl-5-tert-octylphenyl)-2H -benzotriazole, prepared in step a., are placed in a 250 mL flask equipped with a stirrer, thermometer, reflux condenser, Dean-Stark trap and nitrogen inlet. Toluene (100 mL) is added and the mixture is reflux to remove any traces of water. The mixture is then cooled and 0.76 g of oxalyl chloride in 15 mL of toluene is added. The reaction mixture is heated slowly to 60° C. and held at 60–65° C. for eight hours till all the hydrogen chloride is expelled to give the acid chloride title compound.

c. 5-[N,N-Di-n-butylcarbamoyl-2-(2-hydroxy-3-α-cumyl-5-tert-octyl)phenyl]-2H-benzotriazole To a 500 mL flask equipped with a mechanical stirrer, drying tube, thermometer and dropping funnel are added 0.8 g of di-n-butylamine, 6 mL of pyridine and 25 mL of toluene. The mixture is cooled to 0° C. and the acid chloride solution prepared in step b. is placed in the dropping funnel and added to the reaction mixture over a 30-minute period at −5° C. to −10° C. The reaction mixture is stirred at that temperature for 1.5 hours and then held at ambient temperature overnight. The mixture was filtered and then vacuum stripped to give 3.0 g of crude solids. The solid product is chromatographed to provide 1.2 g of the title compound as a tan solid melting at 131–133° C. The structure is confirmed by nmr and mass spectrometry m/z 596.

EXAMPLE 31

5-Trifluoromethyl-2-(2-hydroxy-5-tert-octylphenyl)-2H-benzotriazole

The title compound is prepared according to general procedure of Example 1 the diazo compound of 4-amino-3-nitrobenzotrifluoride and 4-tert-octylphenol, and which is purified by chromatography on silica gel. Recrystallization of the product from either heptane or methanol yields the title compound as a near white solid melting at 80–81° C.

EXAMPLE 32

5-n-Butylthio-2-(2-hydroxy-3,5-di-tert-butylphenyl)-2H-benzotnazole

5-Chloro-2-(2-hydroxy-3,5-di-tert-butylphenyl)2H-benzotriazole (21.2 g, 0.06 mol), n-butyl mercaptan (7.2 g, 0.08 mol), potassium hydroxide (6.7.1 g, 0.12 mol) and N-methylpyrrolidone (50 g, 0.5 mol) are charged to a reactor and heated to 150° C. The reaction mass is held at 150° C. for 4.5 hours at which time it then cooled to ambient temperature. A mixture of 15 g of concentrated hydrochloric acid aand 70 g of ice are then added to the reactor. The solids are filtered off and washed with water. Thirty gram of crude, wet, yellow crystals are obtained as the title compound. This product can be used "as is" in procedure of Example 33.

EXAMPLE 33

5-n-Butylsulfonyl-2-(2-hydroxy-3,5-di-tert-butylphenyl)-2H-benzotriazole

The product as prepared in Example 32 (39.5 g, 0.1 mol), formic acid (10 g, 0.2 mol), sodium tungstate (0.33 g, 0.001 mol) and xylenes (100 mL) are charged to a reactor and heated to 50° C. Hydrogen peroxide (27.2 g, 0.4 mol) is charged dropwise over a one-hour period. The temperature is raised to 75° C. and held there for four hours. The reaction is judged complete using thin layer chromatography. The aqueous layer is split off and the organic phase is washed successively with 100 mL of sodium sulfite solution, twice with sodium bicarbonate solution, with saturated sodium chloride solution and then water. Xylene is stripped off and the crude product is crystallized from ethanol and heptane. Thirty grams of the title compound are obtained as yellow needles melting at 156° C. The structure is verified by $^1$Hnmr analysis.

EXAMPLE 34

2-[2-Hydroxy-3-(di-n-butylaminomethyl)-5-tert-octylphenyl]-2H-benzotriazole

2-[2-Hydroxy-5-tert-octylphenyl]-2H-benzotriazole (30 g, 0.092 mol), paraformaldehyde (3 g, 0.0955 mol) and di-n-butylamine (24.9 g, 0.191 mol) are charged to a pressure reaction at ambient temperature. The reactor is sealed and the temperature raised to 160° C. The reaction mass is held at 160° C. for four hours and then discharged. The reactor is rinsed with toluene. The toluene, amine and water are stripped by rotary evaporation. The crude product is prepared in a 96% yield (40 g). This product is chromatographed on silica gel using a heptane/ethyl acetate gradient as eluent to remove a trace of unreacted starting benzotriazole intermediate. The title compound is a yellow oil whose structure is confirmed by $^1$Hnmr.

EXAMPLE 35

Methylene-[2-(4-tert-octyl-6-2H-benzotriazol-2-yl) phenol]{2'-[4-tert-octyl-6-(5-trifluoromethyl)-2H-benzotriazol-2-yl}phenol}

Trifluoromethyl-2-(2-hydroxy-5-tert-octylphenyl)-2H-benzotriazole (10 g, 0.025 mol, as prepared in Example 31), sodium methoxide (1.49 g, 0.026 mol) and xylenes (20 g, 0.187 mol) are added to a reaction flask which is then heated to 160° C. The compound prepared in Example 34 (11.75 g, 0.0253 mol) dissolved in 11.8 g of xylenes is dripped into the reaction mass over a one-hour period. At the end of the addition, the reaction mass is heated to 205° C. while distilling off xylene, methanol and di-n-butylamine. After one hour at 205° C., the reaction mass is subjected to a 26" Hg vacuum for three hours. After the vacuum is released, the reaction mass is cooled to 100° C. and 100 g of heptane is charged. The solution is then washed with 50 g of 10% aqueous hydrochloric acid followed by 50 g of water. The heptane is dried and the product is crystallized and isolated by filtration. After washing the filter cake with heptane, the product is dried to constant weight in vacuo. The title compound is obtained as a solid (16 g, 87% yield) melting at 163–166° C.

Analysis

Mass spectrometry: 727 (M+H);

$^1$Hnmr (CDCl$_3$): δ0.71 (s, 9H), 0.72 (s, 9H), 1.40 (s, 6H), 1.41 (s, 6H) 1.74 (s, 2H), 1.75 (s, 2H), 4.31 (s, 2H), 7.38 (d, 1H), 7.42 (d, 1H), 7.48 (complex, 2H), 7.68 (dd, 1H), 7.95 (complex, 2H), 8.08 (d, 1H), 8.29–8.33 (3d, 3H), 11.54 (s, 1H)

EXAMPLE 36

5-n-Butylthio-2-(2-hydroxy-3-α-cumyl-5-tert-octylphenyl)-2H-benzotriazole

5-Chloro-2-(2-hydroxy-3-α-cumyl-5-tert-octylphenyl)-2H-benzotriazole (38.1 g, 0.08 mol), n-butyl mercaptan (9 g, 0.10 mol), potassium hydroxide (10.1 g, 0.18 mol) and N-methylpyrrolidone (99 g, 1.0 mol) are charged to a reactor and heated to 170°0C. The reaction mass is held at 170° C. with vigorous stirring for five hours. The reaction is judged as complete using thin layer chromatography. The temperature is reduced to 5° C. and 100 mL of aqueous 2N hydrochloric acid are then added to the reactor. The liquid is decanted and the solids are dissolved in ethyl acetate. The organic layer is washed with aqueous 2N hydrochloric acid followed by water. The ethyl acetate is stripped off and the product is crystallized from ethanol and toluene. The title compound is obtained as a yellow crystalline product in 83% yield. The structure is verified by $^1$Hnmr.

EXAMPLE 37

5-n-Butylsulfonyl-2-(2-hydroxy-3-α-cumyl-5-tert-octylphenyl)-2H-benzotriazole

The product prepared in Example 36 (34.2 g, 0.065 mol), formic acid (6.8 g, 0.13 mol), sodium tungstate (0.21 g, 0.00065 mol) and xylenes (100 mL) are charged to a reactor and heated to 50° C. Hydrogen peroxide (17.7 g, 0.26 mol) is charged dropwise over a one-hour period. After the addition is complete, the reaction mass is held at 50° C. for 3.5 hours. The reaction is judged complete using thin layer chromatography. The reaction mass is washed with 230 g of 14% sodium sulfite solution after the addition of 200 mL of xylene. The organic phase is washed with 200 mL of saturated sodium bicarbonate solution, with 100 mL of saturated sodium chloride solution and then with 200 mL of water. Xylene is stripped off to give a yellow oil which crystallized. The crude product is recrystallized from toluene/methanol to give a 55% yield of the title compound as a solid melting at 118° C. The structure is verified by $^1$Hnmr and mass spectrometry analysis.

EXAMPLE 38

Methyl 3-(Trifluoromethyl-2H-benzotriazol-2-yl)-5-tert-butyl-4-hydroxyhydrocinnamate The general procedure of Example 1, parts a and b, is followed to prepare the unisolated, solid, monoazo intermediate of the title compound from 62.5 g of 4-amino-3-nitrobenzotrifluoride (=4-trifluoromethyl-o-nitroaniline).

The monoazo intermediate (84 g, 0.19 mol), xylenes (116 g, 1.08 mol), diethylamine (100 g, 1.4 mol) and 5% palladium on charcoal (0.5 g, 50% assay) are charged to a reactor. Hydrazine (27.4 g, 0.56 mol) is dripped in over a two-hour period at a temperature range of 15–45° C. After the addition is complete, the temperature is raised to 80° C. and held there for three hours. The reaction is judged complete by thin layer chromatography. The catalyst is removed by filtration and the solvent removed in vacuo to yield 36 grams of the product. After recrystallization from methanol, the title compound is obtained as light yellow needles melting at 105–107° C.

Analysis

Mass spectrometry: 422 (M+H);
$^1$Hnmr (CDCl$_3$): δ1.51 (s, 9H), 2.71 (t, 2H), 3.02 (t, 2H), 3.71 (s, 3H), 7.26 (d, 1H), 7.69 (dd, 1H), 8.07 (d, 1H), 8.17 (d, 1H), 11.55 (s, 1H)

EXAMPLE 39

3-(5-Trifluoromethyl-2H-benzotriazol-2-yl)-5-tert-butyl-4-hydroxyhydrocinnamic Acid The ester prepared in Example 38 (36 g, 0.088 mol), sodium hydroxide (16.4 g, 0.41 mol), N-methylpyrrolidone (12 g, 0.12 mol) and water (400 g) are charged to a reactor and heated to 100° C. The solution is refluxed for three hours after which the reaction mass is poured into 500 g of 10% aqueous hydrochloric acid. The solids are removed by filtration, washed with water and dried to a constant weight to give 31.6 g of product. This material is recrystallized from toluene/acetone to give the title compound as a light yellow solid melting at 166° C.

Analysis

Mass spectrometry: 406 (M–H);
$^1$Hnmr (CDCl$_3$): δ1.50 (s, 9H), 2.78 (t, 2H), 3.04 (t, 2H), 7.26 (d, 1H), 7.65 (dd, 1H), 8.07 (d, 1H), 8.18 (d, 1H), 8.31 (d, 1H), 11.58 (s, 1H)

EXAMPLE 40

Isooctyl 3-(Trifluoromethyl-2H-benzotriazol-2-yl)-5-tert-butyl-4-hydroxyhydrocinnamate The acid prepared in Example 39 (8 g, 0.02 mol), EXXAL® 8 (isooctanol isomers, Exxon, 5 g, 0.038 mol), p-toluenesulfonic acid hydrate (0.5 g, 0.0026 mol) and xylenes (100 mL) are charged to a reactor and refluxed for six hours. TLC shows when the reaction is complete. The solvent is removed and the resulting oil is chromatographed on silical gel. The title compound is obtained in 99.5% yield as a light yellow oil.

Analysis

Mass spectrometry: 520 (M+H);
$^1$Hnmr (CDCl$_3$): δ0.73–1.79 (broad complex, 15H), 1.51 (s, 9H), 2.71 (t, 2H), 3.02 (t, 2H), 4.10 (complex, 2H), 7.27 (d, 1H), 7.69 (dd, 1H), 8.08 (d, 1H), 8.18 (d, 1H), 8.30 (s, 1H), 11.55 (s, 1H)

EXAMPLE 41

5-Trifluoromethyl-2-(2-hydroxy-3,5-di-tert-octylphenyl)-2H-benzotriazole

Following the general procedure of Example 1, 62.5 g of 4-amino-3-nitro-benzotrifluoride is used to make 42.5 g of the title compound which is obtained as yellow crystals melting at 100.5–101.5° C.

Analysis $^1$Hnmr (CDCl$_3$): δ0.79 (s, 18H), 1.45 (s, 9H), 1.54 (s, 3H), 1.56 (s, 3H), 1.82 (s, 2H), 2.12 (s, 2H), 7.44 (d, 1H), 7.66 (dd, 1H), 8.10 (d, 1H), 8.30 (s, 1H), 8.32 (s, 1H), 11.55 (s, 1H)

EXAMPLE 42

5-Trifluoromethyl-2-(2-hydroxy-3-allyl-5-tert-octyl-phenyl)-2H-benzotriazole

The compound prepared in Example 31 (13.01 g, 0.033 mol), potassium hydroxide (2.37 g, 0.036 mol) and ethanol (60 mL) are charged to a reactor and stirred at ambient temperature for two hours. Allyl bromide (4.84 g, 0.039 mol) and potassium iodide (0.34 g, 0.002 mol) are added to the reaction mixture which is heated to 85° C. After holding at 85° C. for 4.5 hours, the solvent is removed and replaced with 100 mL of heptane. The mixture is washed thrice with 40 mL of water. The solvent is then removed to yield 14.2 g of the corresponding O-allyl ether as an off-white solid.

Analysis $^1$Hnmr (CDCl$_3$): δ0.78 (s, 9H), 1.41 (s, 6H), 1.77 (s, 2H), 4.60–4.65 (d, 2H), 5.16–5.34 (m, 2H), 5.86–6.00 (m, 1H), 7.06–7.11 (d, 1H), 7.49–7.54 (dd, 1H),7.61–7.67 (m, 2H), 8.08–8.12 (d, 1H), 8.35 (s, 1H)

The O-allyl compound (14.2 g) as prepared above is charged to a reactor and heated to 190–195° C. and held at that temperature for five hours. Flash column chromatography with silica gel and ethyl acetate/heptane solvent as eluent to give the title compound in 12.2 g yield as a yellow oil.

Analysis

Mass spectrometry: 432 (M+H);
$^1$Hnmr (CDCl$_3$): δ0.78 (s, 9H), 1.46 (s, 6H), 1.81 (s, 2H), 3.53–3.64 (d, 2H), 5.06–5.20 (m, 2H), 6.02–6.18 (m, 1H), 7.29–7.34 (d, 1H), 7.66–7.72 (dd, 1H), 8.05–8.12 (d, 1H), 8.29–8.35 (m, 2H), 11.17 (s, 1H)

EXAMPLE 43

2,2'-Methylene-bis[6-(5-triuoromethyl-2H-benzotriazol-2-yl)-4-tert-octylphenol]

The compound prepared in Example 31 (7.0 g, 0.018 mol), paraformaldehyde (0.29 g, 0.0093 mol) and di-n-butylamine (2.43 g, 0.0186 mol) are charged to a reaction and which is then sealed. The temperature is increased to 160° C. and held there for four hours. The reaction mass is cooled to 110° C. at which time sodium methoxide (0.16 g, 0.0028 mol) is added. The reaction mixture is then heated to 205° C. and held there for three hours. The reaction mass is then cooled to 110° C. and 100 mL of xylenes are added. The reaction mass is neutralized with 10% aqueous hydrochloric acid and the organic phase is twice washed with water. Xylene is then distilled off and replaced with heptane. After cooling the heptane solution, yellow crystals separate out and are isolated by filtration. After drying to constant weight, the title compound (5 g) is obtained as a solid melting at 178° C.

Analysis $^1$Hnmr (CDCl$_3$): δ0.72 (s, 18H), 1.41 (s, 12H), 1.75 (s, 4H), 4.31 (s, 2H), 7.42 (d, 2H), 7.68 (dd, 2H), 8.08 (d, 2H), 8.31 (d, 4H), 11.25 (s, 2H)

EXAMPLE 44

2-(2-Hydroxy-5-trifluoromethylphenyl)-2H-benzotriazole

The title compound is prepared following the general procedure of Example 1 starting with o-nitroaniline and 4-trifluoromethylphenol. Rigorous purification of the crude product on silica gel (heptane/ethyl acetate 4:1) followed by recrystallization from heptane yields the title compound as a yellow solid melting at 119–120° C. The structure is confirmed by UV spectroscopy, mass spectrometry and $^1$Hnmr.

Analysis

Mass spectrometry: m/z 279;

$^1$Hnmr (300 mHz, CDCl$_3$): δ7.31 (d, 1H), 7.54 (m, 2H), 7.61 (dd, 1H), 7.97 (m, 2H), 8.74 (d, 1H), 11.75 (s, 1H)

UV Absorption (ethyl acetate) $\lambda_{max}$ 328, ϵ20,500

EXAMPLE 45

5-Trifluoromethyl-2-[2-hydroxy-3-tert-butyl-5-(3-hydroxypropyl)phenyl]-2H-benzotriazole The title compound is prepared by reacting the ester compound of Example 38 with lithium aluminum hydride according to the procedure of Example 19 of U.S. Pat. No. 5,280,124. The title compound is obtained in 80% yield as a solid melting at 90–91° C.

EXAMPLE 46

5-Trifluoromethyl-2-[2-hydroxy-3-tert-butyl-5-(3-methacryloyloxypropyl)phenyl]-2H-benzotriazole The title compound is prepared by the reaction of the compound of Example 45 with methacryloyl chloride in the presence of tniethylamine in toluene.

EXAMPLE 47–53

Following the general procedure of Example 45, the following compounds of formula III are prepared where n is 1, m is 2 and $E_5$ is hydroxy.

| Example | G$_1$ | G$_2$ | E$_1$ | E$_3$ |
|---|---|---|---|---|
| 47 | Cl | F | tert-butyl | — |
| 48 | H | CF$_3$ | phenyl | — |
| 49 | H | CF$_3$ | allyl | — |

-continued

| Example | G$_1$ | G$_2$ | E$_1$ | E$_3$ |
|---|---|---|---|---|
| 50 | H | CN | α-cumyl | — |
| 51 | H | E$_3$SO | α-cumyl | butyl |
| 52 | H | E$_3$SO$_2$ | phenyl | phenyl |
| 53 | H | E$_3$SO$_2$ | tert-octyl | ethyl |

EXAMPLE 54

5-Trifluoromethyl-2-[2-hydroxy-3-tert-butyl-5-(2-hydroxyethyl)phenyl]-2H-benzotriazole When using the general procedure of Example 1 the 2-α-cumyl-4-tert-octylphenol is replaced by 2-tert-butyl-4-(2-hydroxyethyl)phenol, the title compound is prepared.

EXAMPLE 55

5-Trifluoromethyl-2-[2-hydroxy-5-(2-hydroxyethyl)phenyl]-2H-benzotriazole

When using the general procedure of Example 1, the 2-α-cumyl-4-tert-octylphenol is replaced by 4-(2-hydroxyethyl)phenol, the title compound is prepared.

EXAMPLE 56

5-Trifluoromethyl-2-(2-hydroxy-3,5-di-α-cumylphenyl)-2H-benzotriazole

When using the general procedure of Example 1, the 2-α-cumyl-4-tert-octylphenol is replaced by 2,4-di-α-cumylphenol, the title compound is prepared.

EXAMPLE 57

5-Trifluoromethyl-2-(2-hydroxy-3,5-di-tert-butylphenyl)-2H-benzotriazole

Using the general procedure of Example 1, 47.1 g of 2,4-di-tert-butylphenol is used to prepare 14.1 g of the title compound as yellow needles melting at 131–133° C.

EXAMPLE 58

5-Trifluoromethyl-2-[2-hydroxy-3-tert-butyl-5-(3-aminopropyl)phenyl]-2H-benzotriazole The title compound is prepared by reacting the amide of the acid compound of Example 39 with lithium aluminum hydride dissolved in diethyl ether according to the general procedure of Example 19 of U.S. Pat. No. 5,280,124.

EXAMPLE 59

5-Trifluoromethyl-2-[2-hydroxy-3-tert-butyl-5-(3-methacryloylaminopropyl)phenyl]-2H-benzotriazole The title compound is prepared by the reaction of the compound of Example 58 with methacryloyl chloride in the presence of triethylamine in toluene.

EXAMPLE 60

Isomeric Mixture of 3-[3-(5-Trifluoromethyl-2H-benzotriazol-2-yl)-5-tert-butyl-4-hydroxyhydrocinnamoyloxy]-2-hydroxypropyl Methacrylate and 2-[3-(5-Trifluoromethyl-2H-benzotriazol-2-yl)-5-tert-butyl4hydroxyhydrocinnamoyloxy]-3-hydroxypropyl Methacrylate Following the general procedure of Example 25 of U.S. Pat. No. 5,280,124, the title compounds are prepared from the acid compound of instant Example 39 and glycidyl methacrylate in the presence of tetrabromoammonium bromide dissolved in toluene.

EXAMPLE 61–73

Following the general procedure of Example 45, the following compounds of formula III are prepared where n is 1, m is 2 and $E_5$ is a mixture of —$OCH_2CHOHCH_2OCOC(CH_3)=CH_2$ and —$OCH(CH_2OH)CH_2OCOC(CH_3)=CH_2$.

| Example | $G_1$ | $G_2$ | $E_1$ | $E_3$ | $G_3$ |
|---|---|---|---|---|---|
| 61 | Cl | F | α-cumyl | — | — |
| 62 | H | $CF_3$ | phenyl | — | — |
| 63 | H | $CF_3$ | hydrogen | — | — |
| 64 | H | $CF_3$ | cyclohexyl | — | — |
| 65 | H | $CF_3$ | tert-octyl | — | — |
| 66 | H | CN | α-cumyl | — | — |
| 67 | H | F | phenyl | — | — |
| 68 | Cl | CN | α-cumyl | — | — |
| 69 | H | $G_3CO$— | α-cumyl | — | methyl |
| 70 | H | $G_3CO$— | phenyl | — | phenyl |
| 71 | H | $E_3SO$ | α-cumyl | hexyl | — |
| 72 | H | $E_3SO_2$ | phenyl | $HOCH_2CH_2$— | — |
| 73 | H | $E_3SO_2$ | phenyl | phenyl | — |

EXAMPLE 74

UV Absorption Data

The following table demonstrates the enhanced absorption of the compounds of the instant invention for wavelengths above 350 nm. While the λ max of the instant compound is not always significantly shifted relative to the unsubstituted benzotriazoles, the absorbance is much greater as seen by the absorbance at λ max. In the following examples the absorbance at 375 nm is reported for 20 mg/l concentrations. This is not the molar extinction values.

| Compound* | λ max nm | ε @ λ max | Absorbance @ 375 nm |
|---|---|---|---|
| Q | 345 | 16,500 | 0.28 |
| U | 362 | 17,300 | 0.50 |
| CC | 359 | 14,100 | 0.42 |
| S | 348 | 15,000 | 0.35 |
| BB | 348 | 14,000 | 0.33 |
| DD | 358 | 15,700 | 0.42 |
| EE | 328 | 20,700 | 0.03 |

*Q is 2-(2-hydroxy-3-α-cumyl-5-tert-octylphenyl)-2H-benzotriazole.
U is 5-phenylsulfonyl-2-(2-hydroxy-3-α-cumyl-5-tert-octylphenyl)-2H-benzotriazole.
CC is 5-butylsulfonyl-2-(2-hydroxy-3-α-cumyl-5-tert-octylphenyl)-2H-benzotriazole.
S is 5-trifluoromethyl-2-(2-hydroxy-3-α-cumyl-5-tert-octylphenyl)-2H-benzotriazole.
BB is 5-trifluoromethyl-2-(2-hydroxy-5-tert-octylphenyl)-2H-benzotriazole.
DD is 5-carbomethyoxy-2-(2-hydroxy-3-α-cumyl-5-tert-octylphenyl)-2H-benzotriazole.
EE is 2-(2-hydroxy-5-trifluoromethylphenyl)-2H-benzotriazole.

It is noted that compound EE, prepared in Example 44, is closely related to the compounds disclosed in Japanese Sho 47-15210 and has poor red region absorbance. This is an unwanted property for the UV absorbers where absorbance in the upper regions (above 350 nm) of the UV spectra are of vital importance.

EXAMPLE 75

Yellowness Color Data

The following examples show the difference in color between some of the instant compounds as measured by a Macbeth Color-Eye instrument at a concentration of 30 mg/100 mL in butyl acetate. This shows the relative color of the benzotriazoles having various substituents in the 5-position of the benzo ring and in the 3- and 5-positions of the phenyl ring. In the table, the compounds are listed by increasing b value. The instrument measures yellowness as b and DE is the corresponding Yellowness Index value.

| Compound* | b | DE |
|---|---|---|
| Q | −0.02 | 0.07 |
| BB | 0.20 | 0.27 |
| FF | 0.54 | 0.72 |
| S | 1.05 | 1.28 |
| DD | 1.85 | 2.25 |
| CC | 2.84 | 3.35 |
| U | 3.75 | 4.42 |

*Q is 2-(2-hydroxy-3-α-cumyl-5-tert-octylphenyl)-2H-benzotriazole.
U is 5-phenylsulfonyl-2-(2-hydroxy-3-α-cumyl-5-tert-octylphenyl)-2H-benzotriazole. (see Example 5)
CC is 5-butylsulfonyl-2-(2-hydroxy-3-α-cumyl-5-tert-octylphenyl)-2H-benzotriazole. (see Example 37)
S is 5-trifluoromethyl-2-(2-hydroxy-3-α-cumyl-5-tert-octylphenyl)-2H-benzotriazole. (see Example 1)
BB is 5-trifluoromethyl-2-(2-hydroxy-5-tert-octylphenyl)-2H-benzotriazole. (see Example 31)
DD is 5-carbomethoxy-2-(2-hydroxy-3-α-cumyl-5-tert-octylphenyl)-2H-benzotriazole. (see Example 29)
FF is isooctyl 3-(5-trifluoromethyl-2H-benzotriazol-2-yl)-5-tert-butyl-4-hydroxyhydro-cinnamate (see Example 40)

The compounds not having an α-cumyl moiety in the 3-position of the phenyl ring have better color than the compounds having such a group at that position.

EXAMPLE 76

Yellowness Color Data

The following example shows the lower color in a polymer resin composition containing benzotriazole substituted with a trifluoromethyl group on the benzo ring compared to a similar benzotriazole substituted by a sulfonyl moiety.

Test additives are dry blended with polycarbonate pellets (MAKROLON® 2608–1000, Bayer) using a Turbula mixer. The dry blends are extruded and pelletized using a single screw extruder operated at 525–550° F. (274–288° C.). The pellets are dried overnight in a vacuum oven and molded into test plaques (2"×2"×0125") using an injection molder operated at 525–550° F. (274–288° C.). The color of the test plaques are measured, as yellowness index values using ASTM D-1925, on ten plaques using a spectrophotometer and the average value reported as seen in the table below.

| Formulation* | Yellowness Index |
|---|---|
| 0.08% Phosphite | 4.5 |
| 0.08% Phosphite plus 0.3% UV absorber BB | 7.9 |
| 0.08% Phosphite plus 0.3% UV absorber P | 7.4 |

*Phosphite is tris(2,4-di-tert-butylphenyl)phosphite.
BB is 5-trifluoromethyl-2-(2-hydroxy-5-tert-octylphenyl)-2H-benzotriazole. (Dee Example 31)
P is 2-(2-hydroxy-3,5-di-α-cumylphenyl)-2H-benzotriazole.

Additives are dry blended with polycarbonate pellets (LEXAN® 141–111N, General Electric) using a turbula mixture. The dry blends are extruded and pelletized using a single screw extruder operated at 525° F. (274° C.). The pellets are dried overnight in a vacuum oven and molded into test plaques (2"×2"×0.125") using an injection molder operated at 525–550° F. (274–288° C.). The color of the test plaques as yellowness index values is measured on eight plaques using a colorimeter and the average value reported below.

| Formulation* | Yellowness Index |
|---|---|
| Unstabilized control | 6.8 |
| 0.3% UV absorber P | 8.2 |
| 0.3% UV absorber J | 7.5 |
| 0.3% UB absorber GG | 13.0 |
| 0.3% alkylsulfonyl benzotriazole | 24.2 |

*P is 2-(2-hydroxy-3,5-di-α-cumylphenyl)-2H-benzotriazole.
J is 2-(2-hydroxy-5-tert-octylphenyl-2H-benzotriazole.
GG is 5-chloro-2-(2-hydroxy-3,5-di-tert-butylphenyl-2H-benzotriazole.

EXAMPLE 77

To ascertain the effect on thermal durability and loss rate from a high solids thermoset acrylic coating of various 2H-benzotriazole UV absorbers substituted by a variety of electron withdrawing and electron donating groups, the following tests are carried out.

A high solids thermoset acrylic clear coat is prepared by mixing an experimental acrylic polyol resin and hexamethoxymethylmelamine (Resimene® 747, Monsanto) at a solids ratio of 60/40. The dodecylbenzene sulfonic acid catalyst (Nacure® 5225; King Industries) is added at 0.70% by weight. A flow aid Modaflow® (Monsanto) is added at 0.25% by weight to form a model acrylic melamine resin system.

The model clear coat is reduced with xylene to a viscosity of 26–27 second using a Zahn #2 cup and applied via a conventional air spray at 50 psi (3.5 Kg/cm$^2$) over a 1"×3" (2.54 cm×7.62 cm) quartz slide. Cure is achieved by baking the slide for 30 minutes at 260° F. (127° C.). The clear coat is stabilized with 1% by weight of a hindered amine light stabilizer, bis-(1-octyloxy-2,2,6,6-tetramethylpiperidin-4-yl)sebacate, (TINUVIN® 123, Ciba-Geigy). The various test benzotriazole UV absorbers are incorporated at the 5 mmol % by weight in the clear coat. The film thickness on the quartz slides range from 1.15 to 1.41 mils (0.029 to 0.036 mm).

The films on the quartz slides are weathered according to the following conditions in Xenon Arc Weather-Ometer with a controlled irradiance at 6500 W, using inner quartz and outer borosilicate S-type filter. The irradiation cycle is as follows: 40 minutes of straight irradiation with no water spray, followed by 20 minutes of light plus front spray, followed by 60 minutes of light irradiation and finally by 60 minutes dart plus rear spray (condensation). The setting is at 0.55 W/M$^2$ at 340 nm, 1.98 kJ/hour. In the light cycle the black panel temperature is controlled at 70±2° C. The relative humidity in the light cycle is in the range of 50–55% and in the dark cycle 100%. The absorbance of the long wavelength UV band as a function of Xenon arc weathering hours are recorded in the table below.

To follow the loss of UV absorbers from the clear coats, UV spectra are measured initially and after weathering at regular time intervals. The UV spectrophotometer measures absorbance linearly up to 5.5 absorbance units using a reference beam attenuation technique.

It is assumed that the degradation products from the UV absorber do not contribute to the UV spectrum. This is tested by following the ratio of absorbance of the band at about 300 nm and the band at about 340 nm. The ratio does not change upon weathering the sample, This suggests that the UV spectrum of the weathered films correspond to the amount of UV absorber remaining in the film with very little if any contribution to the spectrum by photo degradants.

The data in the table below are based on formula A after 1211 hours of exposure of the clear coats containing the test benzotriazole UV absorbers.

| Compound | Units Absorbance Loss | $G_2$ | $E_1$ | $E_2$* |
|---|---|---|---|---|
| A | 1.7982 | hydrogen | —PO(OEt)$_2$ | tert-octyl |
| B | 1.6300 | hydrogen | nitro | tert-octyl |
| C | 1.4863 | phenyl-S— | tert-butyl | group I |
| D | 1.4002 | hydrogen | hydrogen | group II |
| E | 1.1872 | methoxy | tert-butyl | methyl |
| F | 0.5259 | hydrogen | tert-butyl | group II |
| G | 0.4527 | hydrogen | hydrogen | α-cumyl |
| H | 0.4420 | hydrogen | tert-butyl | group I |
| I | 0.4299 | hydrogen | tert-octyl | α-cumyl |
| J | 0.4134 | hydrogen | hydrogen | tert-octyl |
| K | 0.3777 | hydrogen | tert-octyl | tert-octyl |
| L | 0.3712 | hydrogen | tert-butyl | CH$_2$CH$_2$CH$_2$OH |
| M | 0.3433 | hydrogen | α-cumyl | group II |
| N | 0.3098 | cyano | tert-butyl | tert-butyl |
| O | 0.2689 | phenyl-SO$_2$— | tert-butyl | group I |
| P | 0.2576 | hydrogen | α-cumyl | α-cumyl |
| Q | 0.2492 | hydrogen | α-cumyl | tert-octyl |

*Group I is —CH$_2$CH$_2$COOC$_8$H$_{17}$
Group II is —CH$_2$CH$_2$COOCH$_3$

Inspection of these data leads to some clear conclusions about the photostability of 2H-benzotriazole UV absorbers and about the nature of the substitution which will affect that photostability.

Increased photostability occurs when $E_1$ is α-cumyl or phenyl and when $G_2$ is an electron withdrawing group such as phenyl-sulfonyl or cyano.

The nature of the $E_2$ group has less influence on the photostability of the benzotriazole UV absorbers.

From these observations, then an idealized benzotriazole UV absorber might theoretically be designed where $G_2$ is an electron withdrawing group, $E_1$ is an effective bulky group, and $E_2$ is a thermally stable moiety. One such idealized compound might be a benzotriazole where $G_2$ is phenylsulfonyl, $E_1$ is α-cumyl and $E_2$ is tert-octyl. This benzotriazole is generically claimed in U.S. Pat. No. 5,280,124. The data given in Example 78 below confirms this prediction and this "idealized" compound does indeed exhibit a very low loss rate well below the present state of the art.

EXAMPLE 78

This example demonstrates the superior durability of benzotriazoles substituted at the 5-position of the benzo ring.

Following the general procedure of Example 77, a number of additional benzotriazole test compounds are incorporated into a high solids thermoset acrylic melamine resin at such concentrations between 1.93 and 3% by weight to give equal molar concentrations of test benzotriazole in equal film thickness, and sufficient to give a starting absorbance of approximately 2.0 absorbance units.

The test discs are exposed in a Xenon-Arc Weather-Ometer at X180 cycle (0.45 Watts/M$^2$). The initial UV absorbance is measured followed by measurements at roughly 250 hour intervals for the first 2000 hours and every 500 hours thereafter. Each clear coat also contains 1% by weight of a hindered amine light stabilizer, bis-(1-octyloxy-2,2,6,6-tetramethylpiperidin- 4-yl) sebacate, as well.

The data in the table below are based on compounds of formula A after 1253 hours of exposure of the clear coats containing the test benzotriazole UV absorbers.

| Compound | Units Absorbance Loss | $G_2$ | $E_1$ | $E_2$ |
| --- | --- | --- | --- | --- |
| R | 0.2424 | hydrogen | phenyl | α-cumyl |
| Q | 0.2351 | hydrogen | α-cumyl | tert-octyl |
| S | 0.1271 | $CF_3$ | α-cumyl | tert-octyl |
| T | 0.1827 | phenyl-$SO_2$ | tert-butyl | tert-butyl |

The data in the table below are based on compounds of formula A after 1489 hours of exposure of the clear coats containing the test benzotriazole UV absorbers.

| Compound | Units Absorbance Loss | $G_2$ | $E_1$ | $E_2$ |
| --- | --- | --- | --- | --- |
| R | 0.3724 | hydrogen | phenyl | α-cumyl |
| Q | 0.287 | hydrogen | α-cumyl | tert-octyl |
| S | 0.1547 | $CF_3$ | α-cumyl | tert-octyl |
| T | 0.2654 | phenyl-$SO_2$ | tert-butyl | tert-butyl |

The data in the table below are based on compounds of formula A after 2521 hours of exposure of the clear coats containing the test benzotriazole UV absorbers.

| Compound | Units Absorbance Loss | $G_2$ | $E_1$ | $E_2$ |
| --- | --- | --- | --- | --- |
| R | 0.4824 | hydrogen | phenyl | α-cumyl |
| Q | 0.4054 | hydrogen | α-cumyl | tert-octyl |
| S | 0.2192 | $CF_3$ | α-cumyl | tert-octyl |
| T | 0.3570 | phenyl-$SO_2$ | tert-butyl | tert-butyl |

It is clear from the three tables above that Compounds S and especially T which have an electron withdrawing group at the 5-position of the benzo ring are significantly more durable than benzotriazoles which do not have such a group on the benzo ring.

The data in the table below are based on compounds of formula A after 1264 hours of exposure of the clear coats containing the test benzotriazole UV absorbers.

| Compound | Units Absorbance Loss | $G_2$ | $E_1$ | $E_2$ |
| --- | --- | --- | --- | --- |
| Q | 0.2293 | hydrogen | α-cumyl | tert-octyl |
| S | 0.0921 | $CF_3$ | α-cumyl | tert-octyl |
| T | 0.1965 | phenyl-$SO_2$ | tert-butyl | tert-butyl |
| U | 0.0944 | phenyl-$SO_2$ | α-cumyl | tert-octyl |
| V | 0.1719 | chloro | α-cumyl | tert-octyl |
| W | 0.1655 | fluoro | α-cumyl | tert-octyl |
| X | 0.1796 | hydrogen | phenyl | tert-octyl |

The data in the table below are based on compounds of formula A after 1518 hours of exposure of the clear coats containing the test benzotriazole UV absorbers.

| Compound | Units Absorbance Loss | $G_2$ | $E_1$ | $E_2$ |
| --- | --- | --- | --- | --- |
| Q | 0.2662 | hydrogen | α-cumyl | tert-octyl |
| S | 0.1116 | $CF_3$ | α-cumyl | tert-octyl |
| T | 0.2423 | phenyl-$SO_2$ | tert-butyl | tert-butyl |
| U | 0.1114 | phenyl-$SO_2$ | α-cumyl | tert-octyl |
| V | 0.1955 | chloro | α-cumyl | tert-octyl |
| W | 0.1668 | fluoro | α-cumyl | tert-octyl |
| X | 0.2220 | hydrogen | phenyl | tert-octyl |

The data in these tables clearly show that benzotriazoles substituted by an electron withdrawing group on the benzo ring, particularly a group such as trifluoromethyl, fluoro or phenylsulfonyl, are especially durable as measured by low loss rate absorbance values after exposure to acetonic radiation. Compounds S, U, V and W are especially durable and fit the profile proposed above. Indeed, the prediction that Compound U would be particularly durable is borne out by the data above. Inspection of the data for compounds T and U shows the added beneficial effect of having an effective bulky group such as α-cumyl at the $R_1$ position compared to a mere alkyl moiety such as tert-butyl at that position.

EXAMPLE 79

This example demonstrates the lack of durability of a representative benzotriazole substituted by an electron donating group on the phenoxy ring relevant to a commercial benzotriazole in a coating composition.

Following the general procedure of Example 77, representative benzotriazole test compounds are incorporated into a high solids thermoset acrylic melamine resin at concentrations between 1.93 and 3% by weight to give equal molar concentrations of the test benzotriazole in equal film thickness and sufficient to give a starting absorbance of approximately 2.0 absorbance units. The test samples are exposed as described in Example 77 for 1002 hours.

| Compound* | Units of Absorbance Loss |
|---|---|
| Q | 0.28 |
| Z | 1.58 |

*Q is 2-(2-hydroxy-3-α-cumyl-5-tert-octylphenyl)-2H-benzotriazole.
Z is 2-(2-hydroxy-4-n-butoxyphenyl)-2H-benzotriazole.

It is clear that the presence of an electron donating group on the phenoxy ring of the benzotriazole adversely affects the durability of said benzotriazole.

EXAMPLE 80

The durability of representative benzotriazoles in thermoplastic substrates is determined by incorporating various test compounds into solvent cast films of poly(vinyl chloride), polycarbonate and polystyrene resins. The free standing films are mounted into cardboard holders, secured in metal frames and exposed in an Atlas C165 Xenon-arc Weather-Ometer under dry conditions according to ASTM G26 for 1100 and 2200 hour exposure. Loss of UV absorber is determined by monitoring the loss of diagnostic UV absorption as described earlier. Performance is measured by a change in color or the physical integrity of the film.

Polycarbonate flake (LEXAN® 145, General Electric) is dissolved in methylene chloride at room temperature along with between 1 and 3% by weight of test benzotriazole, based on the polycarbonate. Films are cast using a calibrated drawdown bar to prepare 1 mil thick film after drying.

The following test data show the increase in durability obtained with a benzotriazole substituted on the 5-position of the benzo ring with an alkylsulfonyl moiety. These results mirror those obtained with coating results.

| | Absorbance (max) | | | |
|---|---|---|---|---|
| Compound* (wt %) | 0 hrs | 1100 hrs | Loss units | % Loss |
| AA (2.5) | 1.333 (364 nm) | 1.300 | 0.033 | 2.5 |
| P (1.5) | 1.062 (347 nm) | 0.919 | 0.143 | 13.5 |
| P (2.5) | 2.104 | 1.844 | 0.260 | 12.3 |

*AA is 5-nonylsulfonyl-2-(2-hydroxy-3-α-cumyl-5-tert-octylphenyl)-2H-benzotriazole.
P is 2-(2-hydroxy-3,5-di-α-cumylphenyl)-2H-benzotriazole.

EXAMPLE 81

Following the procedure of Example 80, this example shows the increase in polycarbonate film of the durability of a benzottiazole substituted on the benzo ring with a trifluoromethyl moiety in the 5-position after exposure for 2000 hours in the Atlas C165 Weather-meter.

| | Absorbance (max) | | | |
|---|---|---|---|---|
| Compound* (wt %) | 0 hrs | 2000 hrs | Loss units | % Loss |
| BB (2.19) | 2.654 (352 nm) | 2.638 | 0.016 | 0.6 |
| J (1.81) | 2.454 (344 nm) | 2.270 | 0.184 | 7.5 |

*BB is 5-trifluoromethyl-2-(2-hydroxy-5-tert-octylphenyl)-2H-benzotriazole (compound of Example 31).
J is 2-(2-hydroxy-5-tert-octylphenyl)-2H-benzotriazole.

EXAMPLE 82

The data in the following example show the change in color of the polycarbonate films exposed according to the procedure of Example 81 as measured on an ACS spectrophotometer, large area view, spectral component included d/8, 10° observer, with yellowness index measured according to ASTM D1925 after 2000 hours exposure.

These data correlates with the advantages seen for the instant compound in terms of stability and spectral coverage leading to a direct increase in performance of the polycarbonate resin films.

| Compound* (wt %) | Δ Yellowness Index |
|---|---|
| BB (2.19) | 2.9 |
| J (1.81) | 4.0 |

*BB is 5-trifluoromethyl-2-(2-hydroxy-5-tert-octylphenyl)-2H-benzotriazole (compound of Example 31).
J is 2-(2-hydroxy-5-tert-octylphenyl)-2H-benzotriazole.

The test compound BB is discernibly less colored than the prior art compound J.

EXAMPLE 83

The following example shows that the stability increases observed for benzotriazoles bearing an electron withdrawing group in the 5-position of the benzo ring in polar coatings such as thermoset acrylic melamine resins and polycarbonate are also seen in less polar substrates such as poly(vinyl chloride) (PVC).

PVC films of GEON® 27 (Geon Co.) are solvent cast as described above with warm tetrahydrofuran (THF) and exposed in an Atlas C165 Weather-Ometer as described in Example 60 for 1100 hours.

| | Absorbance (max) | | | |
|---|---|---|---|---|
| Compound* (wt %) | 0 hrs | 1100 hrs | Loss units | % Loss |
| AA (2.5) | 1.149 (368 nm) | 1.103 | 0.036 | 3.1 |
| P (1.5) | 1.145 (347 nm) | 1.022 | 0.123 | 10.7 |
| P (2.5) | 2.211 | 2.081 | 0.130 | 5.6 |

*AA is 5-nonylsulfonyl-2-(2-hydroxy-3-α-cumyl-5-tert-octylphenyl)-2H-benzotriazole.
P is 2-(2-hydroxy-3,5-di-α-cumylphenyl)-2H-benzotriazole.

EXAMPLE 84

The following example shows an improvement in color protection of a pigmented polyacetal formulation for a benzotriazole substituted on the 5-position of the benzo ring with a trifluoromethyl moiety.

The test additives are dry blended with polyacetal pellets (DELRIN® 500P NC010, DuPont) using a Turbula mixer. The dry blend is extruded and pelletized using a twin screw extruder at a melt temperature of about 410° F. (210° C.). The pellets are molded into test plaques (2"×2"×0.060") using an injection molder operated at 410–420° F. (204–216° C.). The plaques are exposed in a Xenon-arc Weather-Ometer according to automotive test procedure SAE J1885. Exposure is measured in terms of the total irradiation, measured in kilojoules per square meter ($kJ/m^2$). Color change in the exposed samples is determined by measuring the color of the exposed samples compared to the unexposed samples as color difference ($\Delta E$) according to ASTM D2244. The contents are in weight %.

| Contents* | Control | Test Sample |
|---|---|---|
| Polyacetal | 98.8% | 98.8% |
| Pigment (CHROMOPHTAL ® Red G) | 0.30% | 0.30% |
| Hindered Amine | 0.25% | 0.25% |
| Benzotriazole P | 0.60% | — |
| Benzotriazole S | — | 0.60% |
| ACRAWAX C | 0.05% | 0.05% |
| Color Difference ($\Delta E$) | | |
| after 600 $kJ/m^2$ | 6.8 | 5.8 |
| after 900 $kJ/m^2$ | 11.7 | 10.0 |
| after 1240 $kJ/m^2$ | 22.5 | 20.0 |

*Hindered amine is di(1,2,2,6,6-pentamethylpiperidin-4-yl) 2-butyl-2-(3,5-di-tert-butyl-4-hydroxybenzyl)malonate.
P is 2-(2-hydroxy-3,5-di-α-cumylphenyl)-2H-benzotriazole.
S is 5-trifluoromethyl-2-(2-hydroxy-3-α-cumyl-5-tert-octylphenyl)-2H-benzotriazole.

EXAMPLE 85

The following examples illustrates the superior performance of a benzotriazole substituted on the 5-position of the benzo ring with a trifluoromethyl group in protecting poly(butylene terephthalate) as measured by gloss retention.

The test additives are dry blended with poly(butylene terephthalate) pellets (VALOX® 315–1001, General Electric) using a Turbula mixer. The dry blends are extruded and pelletized using a twin screw extruder at 465–490° C. The pellets are molded into test plaques (2"×2"×0.060") using an injection molder operated at 475–515° F. (246–268° C.). The plaques are exposed in a Xenon arc Weather-Ometer according to ASTM G26 test method A. Gloss is measure at 60° on the unexposed and exposed samples using a glossmeter according to ASTM D523. Gloss retention %=(gloss exposed sample/gloss of unexposed sample)×100. The contents are in weight %.

| Contents* | Control | Test Sample |
|---|---|---|
| Poly(butylene terephthalate) | 98.35% | 98.35% |
| Titanium Dioxide | 1.00% | 1.00% |
| Hindered Phenol | 0.05% | 0.05% |
| Phosphite | 0.10% | 0.10% |
| Benzotriazole P | 0.50% | — |
| Benzotriazole S | — | 0.60% |
| Gloss Retention % | | |
| after 500 hrs exposure | 89% | 94% |
| after 750 hrs exposure | 65% | 82% |

*Hindered phenol is 3,5-dioxaoctamethylene bis(3-methyl-5-tert-butyl-4-hydroxy-hydrocinnamate).
Phosphite is tris(2,4-di-tert-butylphenyl) phosphite.
P is 2-(2-hydroxy-3,5-di-α-cumylphenyl)-2H-benzotriazole.
S is 5-trifluoromethyl-2-(2-hydroxy-3-α-cumyl-5-tert-octylphenyl)-2H-benzotriazole.

EXAMPLE 86

Polystyrene films (crystalline polystyrene obtained from Chevron, free of zinc stearate and mineral oil) are solvent case from solutions in methylene chloride. These films are exposed to UV light as described in Example 80. The samples contain no hindered amine stabilizer and are monitored for color change after 1000 hours exposure, for loss of UV absorber and for physical integrity (cracking or catastrophic film failure). Exposure is stopped after 1500 hours.

| | Exposure 1000 hours and 1500 hours | |
|---|---|---|
| Compound* (wt %) | Yellowness Index | Film Integrity |
| Compound of Example 31 (2.19%) | 6.2 | film intact |
| Compound A | 6.9 | film failed |
| Compound P | 9.2 | film cracking |

*Compound A is 2-(2-hydroxy-5-tert-octylphenyl)-2H-benzotriazole.
Compound P is 2-(2-hydroxy-3,5-diα-cumylphenyl)-2H-benzotriazole.

Products from the polystyrene degradation absorbed in the ultraviolet obscuring attempts at UV absorber measurements. Color data obtained after 1000 hours exposure show the effectiveness of the instant compound of Example 31. After 1500 hours exposure, the films containing compounds A and P show significant film degradation while the film containing the instant compound of Example 31 is still intact.

EXAMPLE 87

Polycarbonate films of about 1 mil thickness and containing a UV absorber are prepared by dissolving polycarbonate granules (LEXAN® 145, General Electric) and UV absorbers in methylene chloride and casting the films on a glass plate using a drawdown bar. The films are exposed for 2000 hours in a Xenon Arc Weather-O-meter according to ASTM G26 test method C and the color change ($\Delta YI$) versus that for unexposed films are recorded.

| Sample* (5% by weight) | $\Delta YI$ |
|---|---|
| Compound B | 6.0 |
| Compound of Example 43 | 4.4 |

*Compound B is 2,2'-Methylene-bis[6-(2H-benzotriazol-2-yl)-4-tert-octylphenol].
Compound of Example 43 is 2,2'-Methylene-bis[6-(5-trifluoromethyl-2H-benzotriazol-2-yl)-4-tert-octylphenol].

The instant compound provides discernibly better color to the polycarbonate composition than Compound B.

EXAMPLE 88

5-Trifluoromethyl-2-[2-hydroxy-3-α-cumyl-5-(2-hydroxyethyl)phenyl]-2H-benzotriazole When using the general procedure of Example 1 the 2-α-cumyl-4-tert-octylphenol is replaced by 2-α-cumyl-4-(2-hydroxyethyl)phenol, the title compound is prepared.

What is claimed is:

1. A composition stabilized against thermal, oxidative or light-induced degradation which comprises
   (a) an organic material subject to thermal, oxidative or light-induced degradation wherein the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups, and
   (b) an effective stabilizing amount of a compound of formula I, III or IV

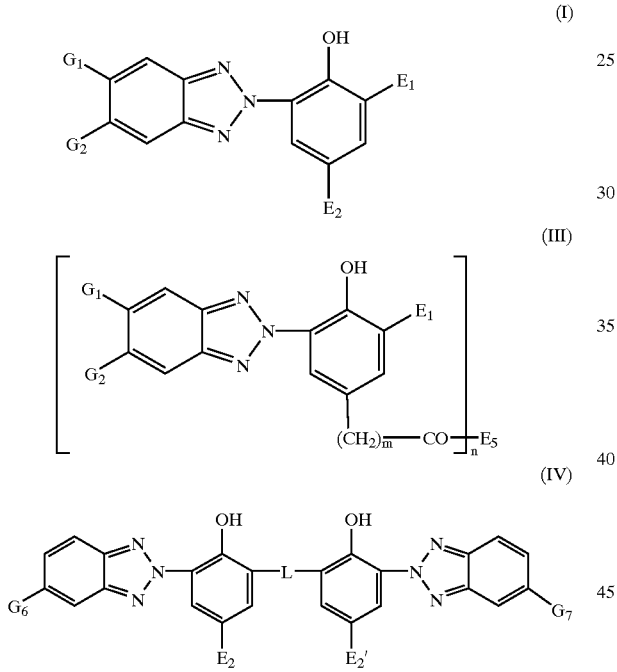

wherein $G_1$ is hydrogen or chloro, $G_2$ is cyano, perfluoroalkyl of 1 to 12 carbon atoms or fluoro, $G_6$ is perfluoroalkyl of 1 to 12 carbon atoms, $G_7$ is hydrogen or perfluoroalkyl of 1 to 12 carbon atoms, $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $E_1$ is alkyl of 1 to 24 carbon atoms substituted by one or two hydroxy groups, $E_2$ and $E_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ and $E_2'$ are independently said alkyl of 1 to 24 carbon atoms or said alkenyl of 2 to 18 carbon atoms substituted by one or more —OH, —OCOE$_{11}$, —OE$_4$, —NCO, —NH$_2$, NHCOE$_{11}$, —NHE$_4$ or —N(E$_4$)$_2$, or mixtures thereof, where $E_4$ is straight or branched chain alkyl of 1 to 24 carbon atoms; or said alkyl or said alkenyl interrupted by one or more —O—, —NH— or —NE$_4$—groups or mixtures thereof and which can be unsubstituted or substituted by one or more —OH, —OE$_4$ or —NH$_2$ groups or mixtures thereof;

n is 1 or 2, when n is 1, $E_5$ is OE$_6$ or NE$_7$E$_8$, or $E_5$ is —PO(OE$_{12}$)$_2$, —OSi(E$_{11}$)$_3$ or —OCO-E$_{11}$, or straight or branched chain C$_1$–C$_{24}$alkyl which is interrupted by —O—, —S—or —NE$_{11}$ and which can be unsubstituted or substituted by —OH or —OCO—E$_{11}$, C$_5$–C$_{12}$ cycloalkyl which is unsubstituted or substituted by —OH, straight chain or branched C$_2$–C$_{18}$alkenyl which is unsubstituted or substituted by —OH, C$_7$–C$_{15}$aralkyl, —CH$_2$—CHOH—E$_{13}$ or glycidyl, $E_6$ is hydrogen, straight or branched chain C$_1$–C$_{24}$alkyl which is unsubstituted or substituted by one or more OH, OE$_4$ or NH$_2$ groups, or —OE$_6$ is —(OCH$_2$CH$_2$)$_w$OH or —(OCH$_2$CH$_2$)$_w$OE$_{21}$ where w is 1 to 12 and $E_{21}$ is alkyl of 1 to 12 carbon atoms, $E_7$ and $E_8$ are independently hydrogen, alkyl of 1 to 18 carbon atoms, straight or branched chain C$_3$–C$_{18}$alkyl which is interrupted by —O—, —S—or —NE$_{11}$—, C$_5$–C$_{12}$cycloalkyl, C$_6$–C$_{14}$aryl or C$_1$–C$_3$hydroxylalkyl, or $E_7$ and $E_8$ together with the N atom are a pyrrolidine, piperidine, piperazine or morpholine ring, $E_5$ is —X—(Z)$_p$—Y—E$_{15}$ wherein X is —O—or —N(E$_{16}$)—, Y is —O—or —N(E$_{17}$)—, Z is C$_2$–C$_{12}$-alkylene, C$_4$–C$_{12}$-alkylene interrupted by one to three nitrogen atoms, oxygen atoms or a mixture thereof, or is C$_3$–C$_{12}$-alkylene, butenylene, butynylene, cyclohexylene or phenylene, each substituted by a hydroxyl group, m is zero, 1 or 2, p is 1, or p is also zero when X and Y are —N(E$_{16}$)— and —N(E$_{17}$)—, respectively, $E_{15}$ is a group —CO—C(E$_{18}$)=C(H)E$_{19}$ or, when Y is —N(E$_{17}$)—, forms together with E$_{17}$ a group —CO—CH=CH—CO—, wherein $E_{18}$ is hydrogen or methyl, and $E_{19}$ is hydrogen, methyl or —CO—X—E$_{20}$, wherein $E_{20}$ is hydrogen, C$_1$–C$_{12}$-alkyl or a group of the formula

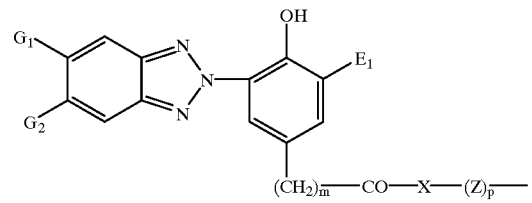

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, when n is 2, $E_5$ is one of divalent radicals —O—$E_9$—O— or —N($E_{11}$)—$E_{10}$—N($E_{11}$)—, $E_9$ is $C_2$–$C_8$alkylene, $C_4$–$C_8$alkenylene, $C_4$alkenylene, cyclohexylene, straight or branched chain $C_4$–$C_{10}$alkylene which is interrupted by —O— or by —CH$_2$—CHOH—CH$_2$—O—$E_{14}$—O—CH$_2$—CHOH—CH$_2$—, $E_{10}$ being straight or branched chain $C_2$–$C_{12}$alkylene which may be interrupted by —O—, cyclohexylene, or

[structure: phenyl—CH$_2$—phenyl]

[structure: cyclohexyl(H)—CH$_2$—cyclohexyl(H)]

or or $E_{10}$ and $E_{11}$ with the two nitrogen atoms form a piperazine ring, $E_{14}$ is straight or branched chain $C_2$–$C_8$alkylene, straight or branched chain $C_4$–$C_{10}$alkylene which is interrupted by —O—, cyclohexylene, arylene or

[structure: phenyl—C(CH$_3$)(CH$_3$)—phenyl]

[structure: cyclohexyl(H)—C(CH$_3$)(CH$_3$)—cyclohexyl(H)]

or where $E_7$ and $E_8$ are independently hydrogen, alkyl of 1 to 18 carbon atoms or $E_7$ and $E_8$ together are alkylene of 4 to 6 carbon atoms, 3-oxapentamethylene, 3-iminopentamethylene or 3-methyliminopentamethylene, $E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, $E_{13}$ is H, straight chain or branched $C_1$–$C_{18}$alkyl which is substituted by —PO(O$E_{12}$)$_2$, phenyl which is unsubstituted or substituted by OH, $C_7$–$C_{15}$aralkyl or —CH$_2$O$E_{12}$, L is alkylene of 1 to 12 carbon atoms, alkylidene of 2 to 12 carbon atoms, benzylidene, p-xylylene, α,α,α',α'-tetramethyl-m-xylylene or cycloalkylidene, and with the proviso that when $G_2$ is —CF$_3$ and $E_1$ is hydrogen, $E_2$ is not methyl.

2. A composition according to claim 1 wherein the resin is a thermoset acrylic melamine resin or an acrylic urethane resin.

3. A composition according to claim 1 wherein component (b) is a compound of formula I

[structure of formula (I): benzotriazole with $G_1$, $G_2$ substituents and phenol ring with OH, $E_1$, $E_2$]

wherein $G_1$ is hydrogen, $G_2$ is cyano, —CF$_3$ or fluoro, $E_1$ is phenylalkyl of 7 to 15 carbon atoms, phenyl, or said phenyl or said phenylalkyl substituted on the phenyl ring by 1 to 4 alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is said alkyl of 1 to 24 carbon atoms or said alkenyl of 2 to 18 carbon atoms substituted by one or more —OH, —OCO$E_{11}$, —O$E_4$, —NCO, —NH$_2$, —NHCO$E_{11}$, —NH$E_4$ or —N($E_4$)$_2$, or mixtures thereof, where $E_4$ is straight or branched chain alkyl of 1 to 24 carbon atoms; or said alkyl or said alkenyl interrupted by one or more —O—, —NH— or —N$E_4$— groups or mixtures thereof and which can be unsubstituted or substituted by one or more —OH, —O$E_4$ or —NH$_2$ groups or mixtures thereof; or is a compound of formula I wherein, $G_1$ is hydrogen, $G_2$ is —CF$_3$ or fluoro, $E_1$ is hydrogen or straight or branched alkyl of 4 to 24 carbon atoms, and $E_2$ is as defined above.

4. A composition according to claim 1 wherein component (b) is a compound of formula IIIA

[structure of formula (IIIA): benzotriazole with $G_1$, $G_2$ substituents and phenol with OH, $E_1$, and —CH$_2$CH$_2$CO—$E_5$ bracketed by n]

wherein $G_1$ is hydrogen, $G_2$ is —CF$_3$ or fluoro, $E_1$ is hydrogen, straight or branched alkyl of 4 to 24 carbon atoms or phenylalkyl of 7 to 15 carbon atoms, $E_5$ is —O$E_6$ or —N$E_7E_8$, or $E_5$ is —X—(Z)$_p$—Y—$E_{15}$ wherein X is —O— or —N($E_{16}$)-, Y is —O— or —N($E_{17}$)-, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is 0, 1, 2 or 3, p is 1, or p is also zero when X and Y are —N($E_{16}$)— and —N($E_{17}$)—, respectively, $E_{15}$ is a group —CO—C($E_{18}$)=C(H)$E_{19}$ or, when Y is —N($E_{17}$)—, forms together with $E_{17}$ a group —CO—CH=CH—CO—, wherein $E_{18}$ is hydrogen or methyl, and $E_{19}$ is hydrogen, methyl or —CO—X—$E_{20}$, wherein $E_{20}$ is hydrogen, $C_1$–$C_{12}$-alkyl or a group of the formula ![structure]

5. A composition according to claim 1 wherein component (b) is a compound of formula IV (IV)

![structure]

wherein $G_6$ is —$CF_3$, $G_7$ is hydrogen or —$CF_3$, $E_2$ and $E_2'$ are independently straight or branched alkyl chain of 1 to 24 carbon atoms. straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; and L is alkylene of 1 to 12 carbon atoms, alkylidene of 2 to 12 carbon atoms, benzylidene, p-xylylene, α,α,α',α'-tetramethyl-m-xylylene or cycloalkylidene.

6. A composition according to claim 1 wherein component (b) is a compound of formula I (I)

![structure]

wherein $G_1$ is hydrogen, $G_2$ is —$CF_3$, $E_1$ is phenylalkyl of 7 to 15 carbon atoms, phenyl, or said phenyl or said phenylalkyl substituted on the phenyl ring by 1 to 4 alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is said alkyl of 1 to 24 carbon atoms or said alkenyl of 2 to 18 carbon atoms substituted by one or more —OH, —OCO$E_{11}$, —$NH_2$ or —NHCO$E_{11}$, or mixtures thereof, or said alkyl or said alkenyl interrupted by one or more —O— and which can be unsubstituted or substituted by one or more —OH, or is a compound of formula I wherein, $G_1$ is hydrogen, $G_2$ is —$CF_3$, $E_1$ is hydrogen, straight or branched alkyl of 4 to 24 carbon atoms or phenylalkyl of 7 to 15 carbon atoms, and $E_2$ is as defined above.

7. A composition according to claim 1 wherein component (b) is a compound of formula IIIA (IIIA)

![structure]

wherein $G_1$ is hydrogen, $G_2$ is —$CF_3$, $E_1$ is hydrogen, straight or branched alkyl of 4 to 24 carbon atoms or phenylalkyl of 7 to 15 carbon atoms, $E_5$ is —$OE_6$ or —$NE_7E_8$ where $E_6$ is hydrogen, straight or branched chain $C_1$–$C_{24}$alkyl which is unsubstituted or substituted by one or more OH groups, or —$OE_6$ is —(OCH$_2$CH$_2$)$_w$OH or —(OCH$_2$CH$_2$)$_w$OE$_{21}$ where w is 1 to 12 and $E_{21}$ is alkyl of 1 to 12 carbon atoms, and $E_7$ and $E_8$ are independently hydrogen, alkyl of 1 to 18 carbon atoms, straight or branched chain $C_3$–$C_{18}$alkyl which is interrupted by —O—, —S— or —$NE_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring.

8. A composition according to claim 1 wherein component (b) is a compound of formula IV (IV)

![structure]

wherein $G_6$ is —$CF_3$, $G_7$ is hydrogen or —$CF_3$,

E₂ and E₂' are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; and L is methylene.

9. A composition according to claim 1 wherein component (b) is
  (a) 5-trifluoromethyl-2-(2-hydroxy-3-α-cumyl-5-tert-octylphenyl)-2H-benzotriazole;
  (b) 5-trifluoromethyl-2-(2-hydroxy-5-tert-octylphenyl)-2H-benzotriazole;
  (c) 5-trifluoromethyl-2-(2-hydroxy-3,5-di-tert-octylphenyl)-2H-benzotriazole;
  (d) 2,2'-methylene-bis[6-(5-trifluoromethyl-2H-benzotriazol-2-yl)-4-tert-octylphenol];
  (e) methylene-2-[4-tert-octyl-6-(2H-benzotriazol-2-yl)phenol]2'-[4-tert-octyl-6-(5-trifluoro-methyl-2H-benzotriazol-2-yl)phenol];
  (f) 3-(5-trifluoromethyl-2H-benzotriazol-2-yl)-5-tert-butyl-4-hydroxyhydrocinnamic acid;
  (g) methyl 3-(5-trifluoromethyl-2H-benzotriazol-2-yl)-5-tert-butyl-4-hydroxy-hydrocinnamate;
  (h) isooctyl 3-(5-trifluoromethyl-2H-benzotriazol-2-yl)-5-tert-butyl-4-hydroxy-hydrocinnamate;
  (i) 5-trifluoromethyl-2-[2-hydroxy-5-(3-hydroxypropyl)phenyl]-2H-benzotriazole;
  (j) 5-trifluoromethyl-2-[2-hydroxy-5-(3-acryloyloxypropyl)phenyl]-2H-benzotriazole;
  (k) 5-trifluoromethyl-2-[2-hydroxy-5-(3-methacryloyloxypropyl)phenyl]-2H-benzotriazole;
  (l) 5-trifluoromethyl-2-[2-hydroxy-5-(3-acrylylaminopropyl)phenyl]-2H-benzotriazole;
  (m) 5-trifluoromethyl-2-[2-hydroxy-5-(3-methacrylylaminopropyl)phenyl]-2H-benzotriazole;
  (n) 5-trifluoromethyl-2-(2-hydroxy-3-α-cumyl-5-tert-butylphenyl)-2H-benzotriazole;
  (o) 5-trifluoromethyl-2-(2-hydroxy-3-α-cumyl-5-nonylphenyl)-2H-benzotriazole;
  (p) 5-trifluoromethyl-2-[2-hydroxy-3-α-cumyl-5-(2-hydroxyethyl)phenyl]-2H-benzo- triazole;
  (q) 5-trifluoromethyl-2-[2-hydroxy-3-α-cumyl-5-(3-hydroxypropyl)phenyl]-2H-benzo- triazole;
  (r) 5-trifluoromethyl-2-(2-hydroxy-3,5-ditert-amylphenyl)-2H-benzotriazole;
  (s) 5-trifluoromethyl-2-(2-hydroxy-3,5-ditert-butylphenyl)-2H-benzotriazole;
  (t) 5-trifluoromethyl-2-(2-hydroxy-3-dodecyl-5-methylphenyl)-2H-benzotriazole;
  (u) 5-trifluoromethyl-2-[2-hydroxy-3-tert-butyl-5-(3-hydroxypropyl)phenyl]-2H-benzotriazole;
  (v) 5-trifluoromethyl-2-(2-hydroxy-3-tert-butyl-5-(2-hydroxyethyl)phenyl]-2H-benzotriazole;
  (w) 5-trifluoromethyl-2-[2-hydroxy-5-(2-hydroxyethyl)phenyl]-2H-benzotnazole;
  (x) 5-trifluoromethyl-2-(2-hydroxy-3,5-di-α-cumylphenyl)-2H-benzotriazole; or
  (y) 5-fluoro-2-(2-hydroxy-3,5-di-α-cumylphenyl)-2H-benzotriazole.

10. A composition according to claim 1 which additionally contains an effective stabilizing amount of at least one other UV absorber selected from the group consisting the benzotriazoles, the s-triazines, hydroxy-benzophenones, the α-cyanoacrylates, the oxanilides and benzoates.

11. A composition according to claim 10 wherein the other benzotriazole is selected from the group consisting of 2-(2-hydroxy-5-methylphenyl)-2H -benzotriazole;
  2-(2-hydroxy-3,5-di-tert-butylphenyl)-2H-benzotriazole;
  2-(2-hydroxy-5-tert-butylphenyl)-2H-benzotriazole;
  2-(2-hydroxy-5-tert-octylphenyl)-2H-benzotriazole;
  5-chloro-2-(2-hydroxy-3,5-di-tert-butylphenyl)-2H-benzotriazole;
  5-chloro-2-(2-hydroxy-3-tert-butyl-5-methylphenyl)-2H-benzotriazole;
  2-(2-hydroxy-3-sec-butyl-5-tert-butylphenyl)-2H-benzotriazole;
  2-(2-hydroxy-4-octyloxyphenyl)-2H-benzotriazole;
  2-(2-hydroxy-3-dodecyl-5-methylphenyl)-2H-benzotriazole;
  2-(2-hydroxy-3,5-di-tert-amylphenyl)-2H-benzotriazole;
  2-[2-hydroxy-3,5-di(α,α-dimethylbenzyl)phenyl]-2H-benzotriazole;
  2-[2-hydroxy-3,(α,α-dimethylbenzyl)-5-tert-octylphenyl]-2H-benzotriazole;
  2-{2-hydroxy-3-tert-butyl-5-[2-omega-hydroxy-octa(ethyleneoxy)carbonyl)ethyl]phenyl}-2H-benzotriazole; and
  2-{2-hydroxy-3-tert-butyl-5-[2-(octyloxy)carbonyl)ethyl]phenyl}-2H- benzotriazole.

12. A composition according to claim 11 wherein the other benzotriazole is 2-(2-hydroxy-3,5-di-tert-amylphenyl)-2H-benzotriazole;
  2-[2-hydroxy-3,5-di(α,α-dimethylbenzyl)phenyl]-2H-benzotriazole;
  2-[2-hydroxy-3-(α,α-dimethylbenzyl)-5-tert-octylphenyl]-2H-benzotriazole;
  2-{2-hydroxy-3-tert-butyl-5-[2-(omega-hydroxy-octa(ethyleneoxy)carbonyl)ethyl]phenyl}-2H-benzotriazole;
  5-chloro-2-(2-hydroxy-3,5-di-tert-butylphenyl)-2H-benzotriazole;
  5-chloro-2-(2-hydroxy-3-tert-butyl-5-methylphenyl)-2H-benzotriazole;
  2-(2-hydroxy-5-tert-octylphenyl)-2H-benzotriazole; or
  2-{2-hydroxy-3-tert-butyl-5-(2-(octyloxy)carbonyl)ethyl]phenyl}-2H- benzotriazole.

13. A composition according to claim 1 which also contains an effective stabilizing amount of a hindered amine.

* * * * *

UNITED STATES PATENT AND TRADEMARK OFFICE
CERTIFICATE OF CORRECTION

PATENT NO.      : 6,458,872 B1
DATED           : October 1, 2002
INVENTOR(S)     : Ramanathan Ravichandran et al.

It is certified that error appears in the above-identified patent and that said Letters Patent is hereby corrected as shown below:

Title page,
Item [60], should read:

--          Related U.S. Application Data
[60]    Division of application No. 09/614,527, filed on Jul. 12, 2000, now Pat. No. 6,262,151, which is a division of application No. 09/234,880, filed on Jan. 21, 1999, now Pat. No. 6,166,218, which is a continuation-in-part of application No. 08/961,127, filed on October 30, 1997, now Pat. No. 5,977,219, which application claims benefit of application 08/745,146, filed on Nov. 7, 1996, which was converted to Provisional application No. 60/367,382. --.

Column 1,
Line 9, after title should read:
-- converted into a Provisional Application Ser. No. 60/367,382 by petition under --

Signed and Sealed this

Twenty-fifth Day of February, 2003

JAMES E. ROGAN
*Director of the United States Patent and Trademark Office*